(12) United States Patent
Knoplioch et al.

(10) Patent No.: US 10,515,721 B2
(45) Date of Patent: *Dec. 24, 2019

(54) AUTOMATED CLOUD IMAGE PROCESSING AND ROUTING

(71) Applicant: General Electric Company, Schenectady, NY (US)

(72) Inventors: Jerome Francois Knoplioch, Buc (FR); Antoine Aliotti, Buc (FR)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/266,745

(22) Filed: Feb. 4, 2019

(65) Prior Publication Data
US 2019/0172576 A1     Jun. 6, 2019

Related U.S. Application Data

(63) Continuation of application No. 15/724,514, filed on Oct. 4, 2017, now Pat. No. 10,198,554, which is a
(Continued)

(51) Int. Cl.
*G06K 9/00* (2006.01)
*G01C 22/00* (2006.01)
(Continued)

(52) U.S. Cl.
CPC .......... *G16H 30/20* (2018.01); *G06F 19/00* (2013.01); *G06F 19/321* (2013.01); *G06K 9/46* (2013.01);
(Continued)

(58) Field of Classification Search
USPC ....... 382/100, 103, 106, 128–133, 155, 162, 382/168, 173, 181, 206, 224, 232, 254,
(Continued)

(56) References Cited

U.S. PATENT DOCUMENTS 8,553,965 B2 * 10/2013 Zhao .................. G06F 9/5072
382/131
8,571,280 B2 * 10/2013 Mathew ............. G06F 19/3418
382/128
(Continued)

OTHER PUBLICATIONS

United States Patent and Trademark Office, "Notice of Allowance", issued in connection with U.S. Appl. No. 14/870,233, dated Jul. 12, 2017, 25 pages.
(Continued)

*Primary Examiner* — Seyed H Azarian
(74) *Attorney, Agent, or Firm* — Hanley, Flight and Zimmerman, LLC

(57) ABSTRACT

Example systems, methods and computer program products for cloud-based, anatomy-specific identification, processing and routing of image data in a cloud infrastructure are disclosed. An example method includes evaluating, automatically by a particularly programmed processor in a cloud infrastructure, image data to identify an anatomy in the image data. The example method includes processing, automatically by the processor, the image data based on a processing algorithm determined by the processor based on the anatomy identified in the image data. The example method also includes routing, automatically by the processor, the image data to a data consumer based on a routing strategy determined by the processor based on the anatomy identified in the image data. The example method includes generating, automatically by the processor based on the processing and routing, at least one of a push of the image data and a notification of availability of the image data.

20 Claims, 14 Drawing Sheets

Related U.S. Application Data continuation of application No. 14/870,233, filed on Sep. 30, 2015, now Pat. No. 9,811,631.

(51) Int. Cl.
*G16H 30/20* (2018.01)
*G06F 19/00* (2018.01)
*H04L 29/08* (2006.01)
*G06K 9/46* (2006.01)

(52) U.S. Cl.
CPC ...... *H04L 67/1097* (2013.01); *G06K 2209/05* (2013.01)

(58) Field of Classification Search
USPC ....... 382/274, 276, 286, 295, 305, 302, 312; 701/26; 345/419; 378/4, 21

See application file for complete search history.

(56) References Cited

U.S. PATENT DOCUMENTS

| | | | |
|---|---|---|---|
| 2013/0155058 A1* | 6/2013 | Golparvar-Fard | G06T 19/006 345/419 |
| 2013/0325244 A1* | 12/2013 | Wang | G05D 1/028 701/26 |
| 2014/0169645 A1* | 6/2014 | Tonti | G06F 19/321 382/128 |
| 2017/0091385 A1 | 10/2017 | Knoplioch et al. | |
| 2018/0046761 A1 | 2/2018 | Knoplioch et al. | |

OTHER PUBLICATIONS

United States Patent and Trademark Office, "Non-Final Office action", issued in connection with U.S. Appl.. No. 14/870,233, dated Mar. 20, 2017, 25 pages.

United States Patent and Trademark Office, "Notice of Allowance", issued in connection with U.S. Appl. No. 15/724,514, dated Sep. 20, 2018, 16 pages.

United States Patent and Trademark Office, "Non-Final office action", issued in connection with U.S. Appl. No. 15/724,514, dated Jun. 14, 2018, 25 pages.

\* cited by examiner

AUTOMATED CLOUD IMAGE PROCESSING AND ROUTING

CROSS-REFERENCE TO RELATED APPLICATIONS

This patent arises from a continuation of U.S. patent application Ser. No. 15/724,514, filed on Oct. 4, 2017, entitled "Automated Cloud Image Processing And Routing", which claims priority as a continuation to U.S. patent application Ser. No. 14/870,233 which was filed on Sep. 30, 2015, entitled "Automated Cloud Image Processing and Routing", each of which is hereby incorporated herein by reference in their entireties.

FEDERALLY SPONSORED RESEARCH OR DEVELOPMENT

[Not Applicable]

MICROFICHE/COPYRIGHT REFERENCE

[Not Applicable]

BACKGROUND

Healthcare entities such as hospitals, clinics, clinical groups, and/or device vendors (e.g., implants) often employ local information systems to store and manage patient information. If a first healthcare entity having a first local information system refers a patient to a second healthcare entity having a second local information system, personnel at the first healthcare entity typically manually retrieves patient information from the first information system and stores the patient information on a storage device such as a compact disk (CD). The personnel and/or the patient then transport the storage device to the second healthcare entity, which employs personnel to upload the patient information from the storage device onto the second information system.

Additionally, modern radiology involves normalized review of image sets, detection of possible lesions/abnormalities and production of new images. Current processing of images, however, is labor-intensive and slow. Consistency of review formats and analysis results is limited by operator availability, skills and variability. Further, a number of processing actions require access to expensive dedicated hardware, which is not easily or affordably obtained.

BRIEF SUMMARY

In view of the above, systems, methods, and computer program products which provide intelligent, anatomy-specific identification, processing, and routing of image data in a cloud infrastructure are provided. The above-mentioned needs are addressed by the subject matter described herein and will be understood in the following specification.

This summary briefly describes aspects of the subject matter described below in the Detailed Description, and is not intended to be used to limit the scope of the subject matter described in the present disclosure.

Certain examples provide a method including evaluating, automatically by a particularly programmed processor in a cloud infrastructure based on receipt at a cloud gateway, image data to identify an anatomy in the image data. The example method includes processing, automatically by the processor, the image data based on a processing algorithm determined by the processor based on the anatomy identified in the image data. The example method also includes routing, automatically by the processor, the image data to a data consumer based on a routing strategy determined by the processor based on the anatomy identified in the image data. The example method includes generating, automatically by the processor based on the processing and routing, at least one of a) a push of the image data and b) a notification of availability of the image data.

Certain examples provide a system including a cloud gateway associated with a cloud infrastructure. The example cloud gateway includes a particularly programmed processor, the cloud gateway configured to receive image data from a data source. The example system also includes an anatomy recognition and routing processor including a particularly programmed processor. The example anatomy recognition and routing processor is configured to evaluate received image data from the cloud gateway to identify an anatomy in the image data. The example anatomy recognition and routing processor is configured to provide the image data to an anatomy processor automatically selected by the anatomy recognition and routing processor from a plurality of anatomy processors. The example plurality of anatomy processors are each configured to process data using an anatomy-specific processing algorithm. The example selected anatomy processor is configured to process the image data and route the image data to a data consumer based on a routing strategy determined by the selected anatomy-specific processor based on the anatomy identified in the image data. In the example system, at least one of a) a push of the image data and b) a notification of availability of the image data is generated based on the processing and routing of the image data.

Certain examples provide a tangible computer readable medium including instructions for execution by a processor, the instructions, when executed, particularly programming the processor to implement a system. The example system includes an anatomy recognition and routing processor configured to evaluate received image data from a cloud gateway to identify an anatomy in the image data. The example anatomy recognition and routing processor is configured to provide the image data to an anatomy processor automatically selected by the anatomy recognition and routing processor from a plurality of anatomy processors. The example plurality of anatomy processors are each configured to process data using an anatomy-specific processing algorithm. The example selected anatomy processor is configured to process the image data and route the image data to a data consumer based on a routing strategy determined by the selected anatomy-specific processor based on the anatomy identified in the image data. In the example system, at least one of a) a push of the image data and b) a notification of availability of the image data is generated based on the processing and routing of the image data.

Figure 1:
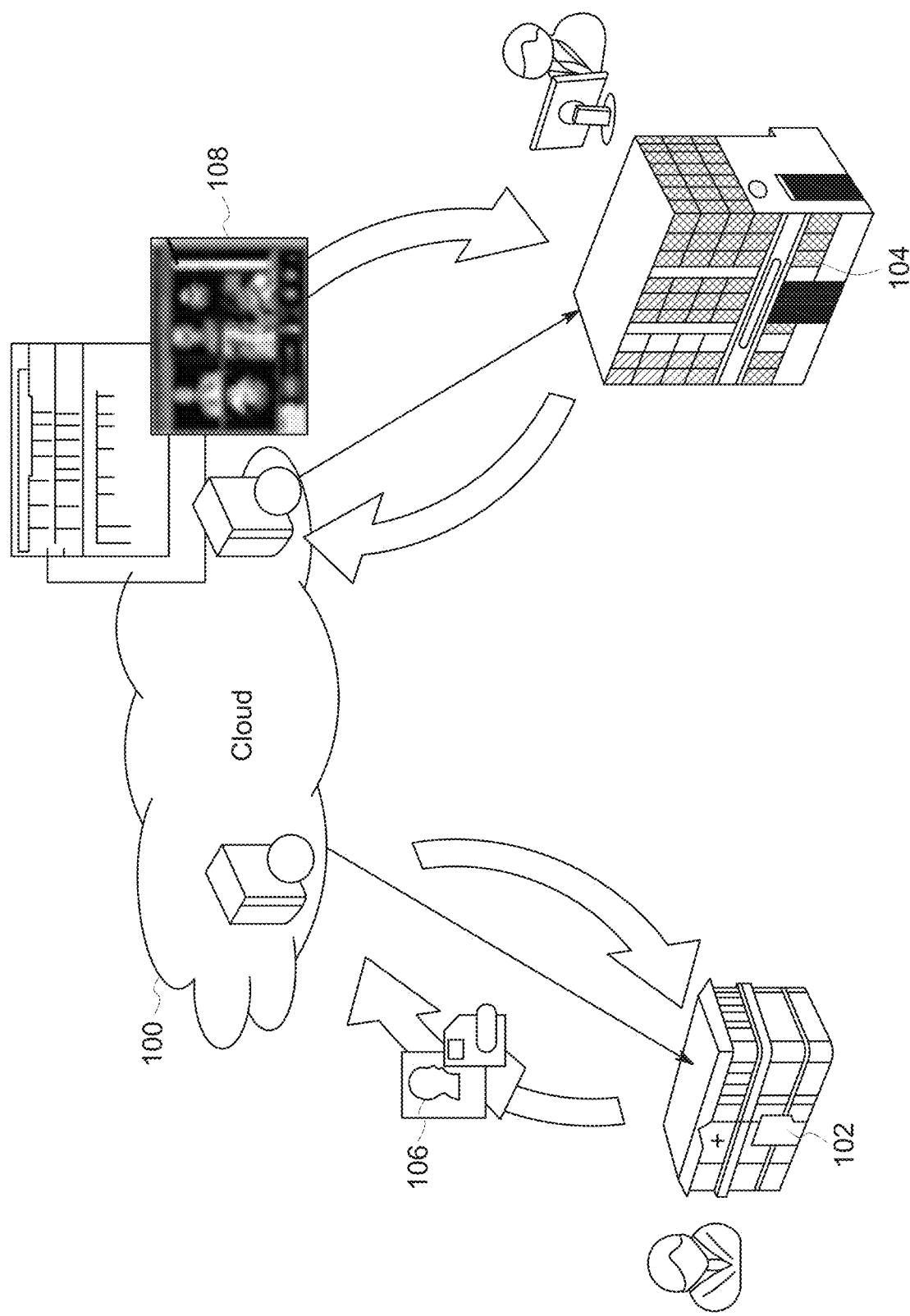
FIG. 1 illustrates an example cloud-based clinical information system employed by a first healthcare entity to share information with a second healthcare entity.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an example implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

Cloud-based clinical information systems and methods of use are disclosed and described herein. An example cloud-based clinical information system described herein enables healthcare entities (e.g., patients, clinicians, sites, groups, communities, and/or other entities) to share information via web-based applications, cloud storage and cloud services. For example, the cloud-based clinical information system may enable a first clinician to securely upload information into the cloud-based clinical information system to allow a second clinician to view and/or download the information via a web application. Thus, for example, the first clinician may upload an x-ray image into the cloud-based clinical information system (and/or the medical image can be automatically uploaded from an imaging system to the cloud-based clinical information system), and the second clinician may view the x-ray image via a web browser and/or download the x-ray image onto a local information system employed by the second clinician.

In some examples, a first healthcare entity may register with the cloud-based clinical information system to acquire credentials and/or access the cloud-based clinical information system. To share information with a second healthcare entity and/or gain other enrollment privileges (e.g., access to local information systems), the first healthcare entity enrolls with the second healthcare entity. In some examples, the example cloud-based clinical information system segregates registration from enrollment. For example, a clinician may be registered with the cloud-based clinical information system and enrolled with a first hospital and a second hospital. If the clinician no longer chooses to be enrolled with the second hospital, enrollment of the clinician with the second hospital can be removed or revoked without the clinician losing access to the cloud-based clinical information system and/or enrollment privileges established between the clinician and the first hospital.

In some examples, business agreements between healthcare entities are initiated and/or managed via the cloud-based clinical information system. For example, if the first healthcare entity is unaffiliated with the second healthcare entity (e.g., no legal or business agreement exists between the first healthcare entity and the second healthcare entity) when the first healthcare entity enrolls with the second healthcare entity, the cloud-based clinical information system provides the first healthcare entity with a business agreement and/or terms of use that the first healthcare entity executes prior to being enrolled with the second healthcare entity. The business agreement and/or the terms of use may be generated by the second healthcare entity and stored in the cloud-based clinical information system. In some examples, based on the agreement and/or the terms of use, the cloud-based clinical information system generates rules that govern what information the first healthcare entity may access from the second healthcare entity and/or how information from the second healthcare entity may be shared by the first healthcare entity with other entities and/or other rules.

In some examples, the cloud-based clinical information system may employ a hierarchal organizational scheme based on entity types to facilitate referral network growth, business agreement management, and regulatory and privacy compliance. Example entity types include patients, clinicians, groups, sites, integrated delivery networks, communities and/or other entity types. A user, which may be a healthcare entity or an administrator of a healthcare entity, may register as a given entity type within the hierarchal organizational scheme to be provided with predetermined rights and/or restrictions related to sending information and/or receiving information via the cloud-based clinical information system. For example, a user registered as a patient may receive or share any patient information of the user while being prevented from accessing any other patients' information. In some examples, a user may be registered as two types of healthcare entities. For example, a healthcare professional may be registered as a patient and a clinician.

In some examples, the cloud-based clinical information system includes an edge device located at healthcare facility (e.g., a hospital). The edge device may communicate with a protocol employed by the local information system(s) to function as a gateway or mediator between the local information system(s) and the cloud-based clinical information system. In some examples, the edge device is used to automatically generate patient and/or exam records in the local information system(s) and attach patient information to the patient and/or exam records when patient information is sent to a healthcare entity associated with the healthcare facility via the cloud-based clinical information system.

In some examples, the cloud-based clinical information system generates user interfaces that enable users to interact with the cloud-based clinical information system and/or communicate with other users employing the cloud-based clinical information system. An example user interface described herein enables a user to generate messages, receive messages, create cases (e.g., patient image studies, orders, etc.), share information, receive information, view information, and/or perform other actions via the cloud-based clinical information system.

In certain examples, images are automatically sent to a cloud-based information system. The images are processed automatically via "the cloud" based on one or more rules. After processing, the images are routed to one or more of a set of target systems.

Routing and processing rules can involve elements included in the data or an anatomy recognition module which determines algorithms to be applied and destinations for the processed contents. The anatomy module may determine anatomical sub-regions so that routing and processing is selectively applied inside larger data sets. Processing rules can define a set of algorithms to be executed on an input data set, for example.

Modern radiology involves normalized review of image sets, detection of possible lesions/abnormalities and production of new images (functional maps, processed images) and quantitative results. Some examples of very frequent processing include producing new slices along specific anatomical conventions to better highlight anatomy (e.g., discs between vertebrae, radial reformation of knees, many musculo-skeletal views, etc.). Additionally, processing can be used to generate new functional maps (e.g., perfusion, diffusion, etc.), as well as quantification of lesions, organ sizes, etc. Automated identification of vascular system can also be processed.

In contrast to labor-intensive, slow, inconsistent traditional processing, a leveraging of cloud resources would open access to large amounts of compute resources and enable automated production of intermediate or final results (new images, quantitative results). It is, however, very difficult to launch the right algorithms automatically. Traditional systems try to guess anatomy and intention of scan from additional information in an image header. Such guesswork is usually very error prone, site dependent and not possible in situations where there is time pressure during scan (trauma, for example). This problem of guesswork also impacts productivity in interactive usages on analysis workstations, Picture Archiving and Communication Systems (PACS), and scanner consoles.

Additionally, high end cloud hardware is expensive to rent, but accessing a larger number of smaller nodes is cost effective compared to owning dedicated, on-premises hardware. Dispatching multiple tasks to a large number of small processing units allows more cost-effective operation, for example.

Although Cloud storage can be an efficient model for long term handling of data, in medical cases, data sets are large and interactive performance from Cloud-based rendering may not be guaranteed under all network conditions. Certain examples desirably push data sets automatically to one or more target systems. Intelligently pushing data sets to one or more target systems also avoids maintaining multiple medical image databases (e.g., Cloud storage may not be an option for sites that prefer their own vendor neutral archive (VNA) or PACS, etc.).

In certain examples, a user is notified when image content is available for routing. In other examples, a user is notified when processing has been performed and results are available. Thus, certain examples provide increases user productivity. For example, results are automatically presented to users, reducing labor time. Additionally, users can be notified when new data is available. Further, large data can be pushed to one or more local systems for faster review, saving networking time. An efficient selection of relevant views also helps provide a focused review and diagnostic, for example. Anatomy recognition results can be used to improve selection of appropriate hanging protocol(s) and/or tools in a final PACS or workstation reading, for example.

Certain examples improve quality and consistency of results through automation. Automated generation of results helps ensure that results are always available to a clinician and/or other user. Routing helps ensures that results are dispatched to proper experts and users. Cloud operation enables access across sites, thus reaching specialists no matter where they are located.

Certain examples also reduce cost of ownership and/or operation. For example, usage of Cloud resources versus local hardware should limit costs. Additionally, dispatching analysis to multiple nodes also reduces cost and resource stress on any particular node.

FIG. 1 illustrates an example cloud-based clinical information system 100 disclosed herein. In the illustrated example, the cloud-based clinical information system 100 is employed by a first healthcare entity 102 and a second healthcare entity 104. As described in greater detail below, example entity types include a community, an integrated delivery network (IDN), a site, a group, a clinician, and a patient and/or other entities.

In the illustrated example, the first healthcare entity 102 employs the example cloud-based clinical information system 100 to facilitate a patient referral. Although the following example is described in conjunction with a patient referral (e.g., a trauma transfer), the cloud-based information system 100 may be used to share information to acquire a second opinion, conduct a medical analysis (e.g., a specialist located in a first location may review and analyze a medical image captured at a second location), facilitate care of a patient that is treated in a plurality of medical facilities, and/or in other situations and/or for other purposes.

In the illustrated example, the first healthcare entity 102 may be a medical clinic that provides care to a patient. The first healthcare entity 102 generates patient information (e.g., contact information, medical reports, medical images, and/or any other type of patient information) associated with the patient and stores the patient information in a first local information system (e.g., PACS/RIS and/or any other local information system). To refer the patient to the second healthcare entity 104, the first healthcare entity posts or uploads an order 106, which includes relevant portions of the patient information, to the cloud-based clinical information system 100 and specifies that the patient is to be referred to the second healthcare entity. For example, the first healthcare entity 102 may use a user interface (FIGS. 9-11) generated via the cloud-based clinical information system 100 to upload the order 106 via the internet from the first local information system to the cloud-based clinical information system 100 and direct the cloud-based information system 100 notify the second healthcare entity 104 of the referral and/or enable the second healthcare entity 104 to access the order 106. In some examples, the cloud-based clinical information system 100 generates a message including a secure link to the order 106 and emails the message to the second healthcare entity 104. The second healthcare entity 104 may then view the order 106 through a web browser 108 via the cloud-based clinical information system 100, accept and/or reject the referral, and/or download the order 106 including the patient information into a second local information system (e.g., PACS/RIS) of the second healthcare entity 104. As described in greater detail below, the cloud-based-based clinical information system 100 manages business agreements between healthcare entities to enable unaffiliated healthcare entities to share information, thereby facilitating referral network growth.

Figure 2:
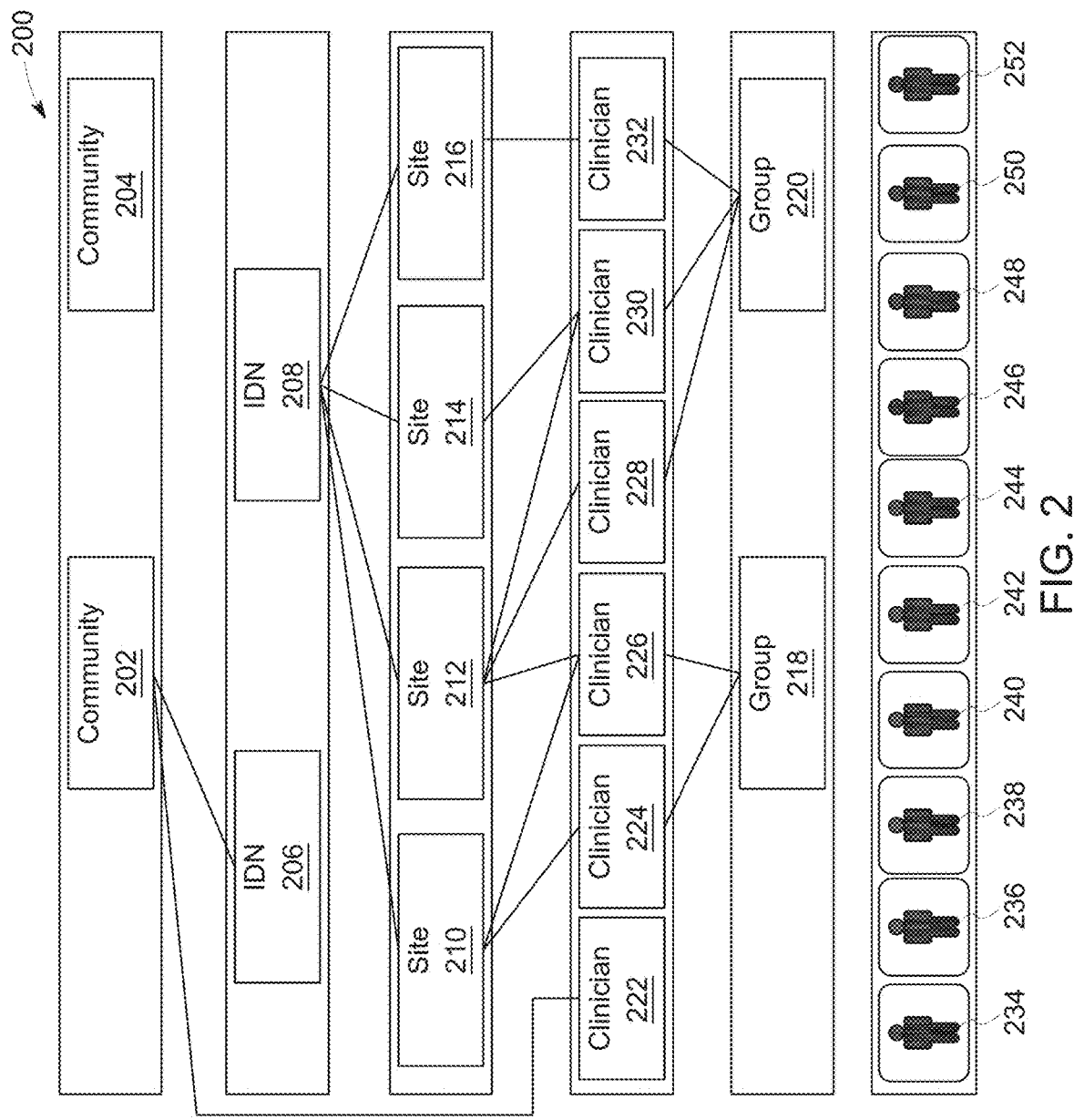
FIG. 2 is a block diagram illustrating an example hierarchal organizational system employed by the example cloud-based clinical information system of FIG. 1.

FIG. 2 illustrates an example hierarchal organization scheme 200 disclosed herein. In some examples, credentials are assigned and/or rules for accessing (e.g., viewing, receiving, downloading, etc.) information and/or sharing (e.g., uploading, sending, etc.) information via the cloud-based clinical information system 100 is governed and/or determined by the cloud-based information system 100 according to the hierarchal organization scheme 200. In the illustrated example, the hierarchal organizational scheme 200 is organized based on entity types. In the illustrated example, the entity types include communities 202, 204, IDNs 206, 208, sites 210, 212, 214, 216, groups 218, 220, clinicians 222, 224, 226, 228, 230, 232, 234, and patients 234, 236, 238, 240, 242, 244, 246, 248, 250, 252. Other examples include other entity types.

In some examples, the communities 202, 204 are legal entities. In some examples, the communities 202, 204 are defined by subject matter (e.g., medical practice type, research area and/or any other subject matter) and/or geographic location. For example, the community 202 may be a plurality of individuals, hospitals, research facilities, etc. cooperating to form a research collaboration.

The IDNs 206, 208 may be a plurality of facilities and/or providers that provide a continuum of care to a market or geographic area. For example, the IDN 206 may be a plurality of medical facilities having business and/or legal relationships.

The sites 210, 212, 214, 216 are medical facilities such as a hospitals, imaging centers and/or any other type of medical facility.

The groups 218, 220 are a plurality of individuals having a legal-based or interest-based relationship. For example, the group 218 may be a limited liability corporation, and the group 220 may be composed of a plurality of clinicians.

Clinicians 222, 224, 226, 228, 230, 232, 234 are healthcare professionals such as physicians, technicians, administrative professionals (e.g., file room clerks, scheduling administrators, reporting administrators, and/or any other administrative professionals), nurses, students, researchers, and/or any other healthcare professionals. In some examples, the clinicians 222, 224, 226, 228, 230, 232, 234 are employed by one or more of the sites 210, 212, 214, 216 and/or the groups 218, 220.

The patients 234, 236, 238, 240, 242, 244, 246, 248, 250, 252 are individuals who will be or have been under the care of one or more of the clinicians 222, 224, 226, 228, 230, 232, 234.

In the illustrated example, credentials and/or rules for accessing and sharing information via the cloud-based clinical information system 100 are assigned and/or governed based on the entity types. Example rules for accessing and sharing information via the cloud-based clinical information system 100 include rules related to regulatory compliance and privacy such as, for example, rules to comply with the Health Insurance Portability and Accountability Act (HIPAA). For example, one of the patients 234, 236, 238, 240, 242, 244, 246, 248, 250, 252 may access his/her patient information from any healthcare entity in communication with the cloud-based clinical information system 100 and share his/her patient information with any healthcare entity in communication with the cloud-based clinical information system 100. However, the cloud-based clinical information system 100 prohibits or prevents the patients 234, 236, 238, 240, 242, 244, 246, 248, 250, 252 from viewing, receiving or sharing other patients' information. In some examples, the cloud-based clinical information system 100 enables the clinicians 222, 224, 226, 228, 230, 232, 234 to view, receive and/or share information related to any of the patients 234, 236, 238, 240, 242, 244, 246, 248, 250, 252 which are under the clinicians' care. However, the cloud-based clinical information system 100 may prevent one of the clinicians 222, 224, 226, 228, 230, 232, 234 from viewing and/or sharing information related to one of the patients 234, 236, 238, 240, 242, 244, 246, 248, 250, 252 not under the clinicians' care.

In some examples, one healthcare entity is a member of one or more other healthcare entities. For example, as illustrated in FIG. 2, the clinician 232 is a member of the group 220 and the site 216. Thus, the clinician 232 may access and/or share information that is accessible to the group 220 and the site 216 and associated with the clinician 232 via the cloud-based clinical information system 100. For example, the clinician 232 may be employed by both the group 220 and the site 216, and the clinician 232 may use the cloud-based clinical information system 100 to access and/or share information related to patients under the care of the clinician 232 at either of the group 220 and the site 216 even if, for example, the group 220 and the site 216 are not affiliated with each other. As described in greater detail below, a first healthcare entity (e.g., the clinician 222) may become a member of second healthcare entity (e.g., IDN 206) by enrolling in the second healthcare entity via the cloud-based clinical information system.

Figure 3:
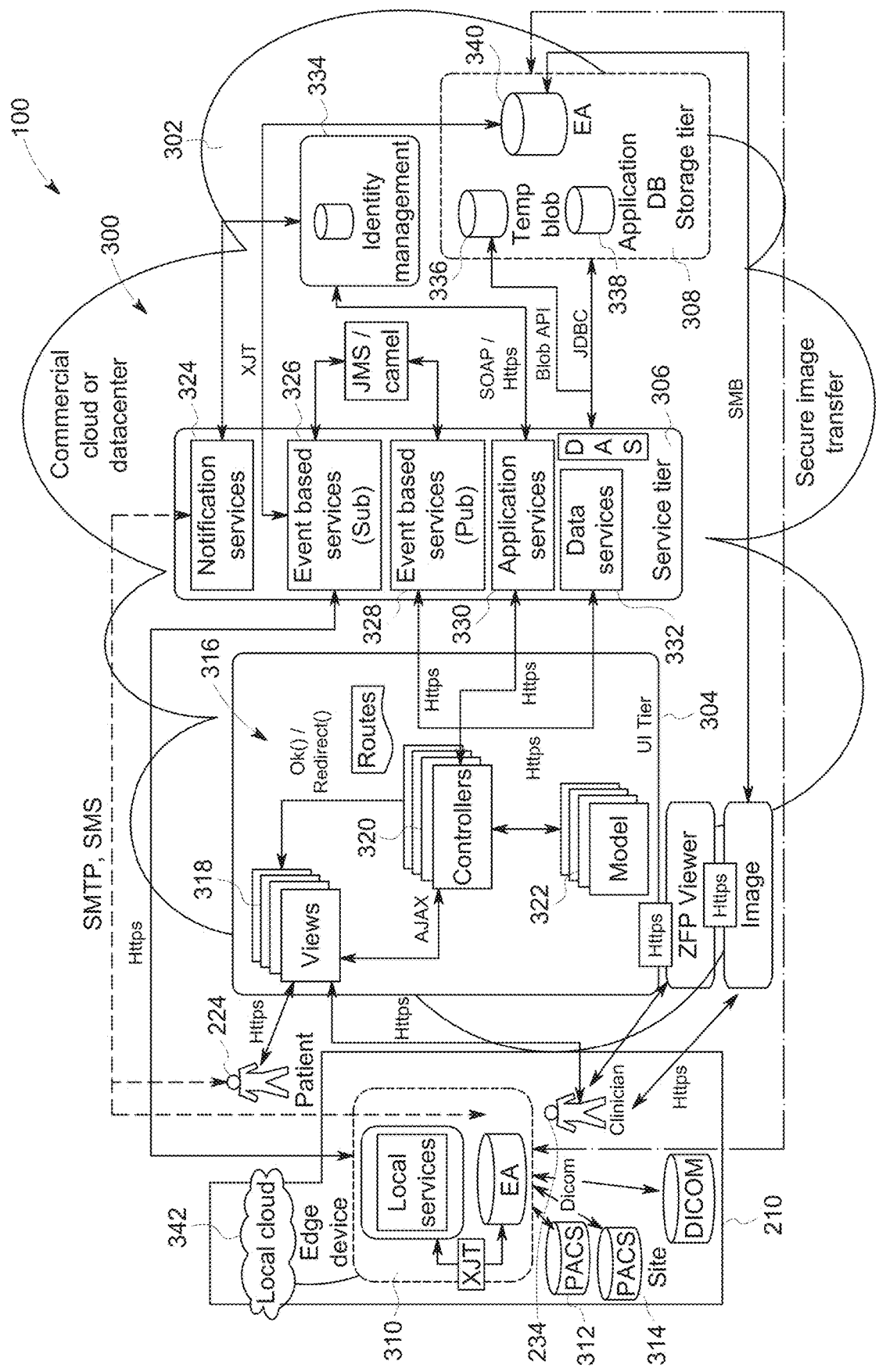
FIG. 3 illustrates an example architecture that may be used to implement the example cloud-based clinical information system of FIG. 1.

FIG. 3 illustrates example architecture 300 to implement the example cloud-based clinical information system 100 of FIG. 1. In the illustrated example, the cloud-based clinical information system 100 includes a remote cloud system 302 ("cloud," "remote cloud") having a web/user interface tier 304, a service tier 306 and a storage tier 308. In the illustrated example, the clinician 234 is located at the site 210. An example edge device 310 is located at the site 234 and facilitates communication between the remote cloud system 302 and local information systems 312, 314 employed by the site 210. For example, the edge device 310 may communicate via Digital Imaging and Communications in Medicine (DICOM) and/or Health Level Seven (HL7) protocols with the local information systems 312, 314 to generate patient and/or exam records in the local information systems 312, 314, retrieve information from the local information system 312, 314 and upload the information into the cloud 300, store information in the local information systems 312, 314, and/or perform other actions. In some examples, the local information systems 312, 314 include picture archiving and communication systems (PACS), electronic health records (EMR) systems, radiology information systems (RIS) and/or other types of local information systems.

In some examples, the web/user interface tier 304 implements a user interface generator to build a user experience. In some examples, the interface generator builds a user experience via model-view-controller architecture 316 including views 318, controllers 320 and models 322. For example, the views 318 request information from the models 322 to generate user interfaces that enable the clinician 234 and/or the patient 224 to view information stored in the remote cloud system 302 via the storage tier 308. In some examples, views 318 generate zero footprint viewers that enable the clinician 234 and/or the patient 224 to view information such as medical images using a web browser. In some examples, the views 318 generate user interfaces that enable the clinician 234 and/or the patient 224 to upload information onto the remote cloud system 302, download information from the remote cloud system 302 onto one or more of the local information systems 312, 314 and/or perform other actions. The example models 322 include underlying data structures that include and/or organize information used by the views 318 to populate the user interfaces. The example controllers 320 request data from the service tier 306, update the models 322 and/or information employed by the models 322 and instruct the views 318 to adjust or change a presentation (e.g., change a screen, scroll, and/or any other adjustment or change to a presentation) provided via the user interfaces.

The example service tier 306 includes notification services 324, event based services 326, 328 employing a publishing-subscribing messaging model, application or web services 330, data services 332, identity management services 334 and/or other services. The example storage tier 308 includes a plurality of storage devices 336, 338, 340 (e.g., databases, blobs, image management and storage devices, and/or any other storage devices). The example notification services 324 generate and communicate (e.g., via email, text message and/or any other way) notifications to users of the example cloud-based clinical information system 100. For example, if the clinician 234 is referred a case via the cloud-based clinical information system 100, the notification services 324 may generate and communicate a text message to a phone associated with the clinician 234 that indicates that information related to the case is accessible via the cloud-based clinical information system 100. The example application services 330 and the identity management services 334 cooperate to provide and/or verify user credentials and/or manage rights associated with healthcare entities, register healthcare entities with the cloud-based clinical information system, enroll healthcare entities with other healthcare entities and/or manage rules related to the healthcare entities accessing and sharing information via the cloud-based clinical information system 100, and/or perform other actions. In some examples, the application services 330 and/or the identity management services 334 implement a registration manager to assign credentials to a healthcare entity to enable the healthcare entity to employ the cloud-based clinical information system 100. In some examples, the credentials grant the healthcare entity access rights and sharing rights to access and share, respectively, healthcare information associated with the healthcare entity via the cloud-based clinical information system. In some examples, the first access rights and the first sharing rights are based on which type of entity is the healthcare entity. For example, if the healthcare entity is registered as a patient, the application services 330 and/or the identity management services 334 may prevent the user from accessing information related to other patients.

In some examples, the application services 330 and/or the identity management services 334 implement an agreement manager to store a contractual agreement between two or more healthcare entities. In some examples, the application services 330 and/or the identity management services 334 implement an enrollment manager to assign rules to a first healthcare entity defining a least one of access rights or sharing rights to healthcare information associated with a second healthcare entity. In some examples, the access or sharing rights are based on the contractual agreement and one or more selections by a user associated with the second healthcare entity. For example, the user associated with the second healthcare entity may prevent the first healthcare entity from sharing the healthcare information, specify which healthcare entities the first healthcare entity may share the health information with via the cloud-based clinical information system, and/or select other access and/or sharing rights. In some examples, the user interface tier 304 and the service tier 306 interact asynchronously. For example, the controllers 320 may communicate a request for information stored in an image management and storage device (e.g., storage device 340) via the data services 332, and the request may be input into a worklist or queue of the service tier 306. Other architectures are used in other examples.

As described in conjunction with FIG. 1 above, the example cloud-based clinical information system 100 may be used to share information between healthcare entities such as the patient 224 and the site 210. For example, the clinician 234 may prepare a medical report and upload the medical report onto the remote cloud system 302 via a user interface generated by the example user interface tier 304. The example notification services 324 may notify the patient 224 that the report is accessible via the cloud-based clinical information system 100, and the patient may use a web browser to view the report via a zero footprint viewer generated by the views 318. In some examples, the application services 330 implements a case history generator to generate a case history related to a patient. For example, the case history generator may attach healthcare information such as a medical report, a message generated by a clinician, etc. to one or more records and/or other healthcare information related to the patient to generate a case history. In some examples, the case history generator attaches information uploaded from a plurality of healthcare entities to a patient record to generate a case history.

In some examples, the cloud-based clinical information system 100 is a hybrid cloud system including the remote cloud system 302 and a local cloud system 342. For example, the cloud-based clinical information system 100 may enable the site 210 to share information with unaffiliated healthcare entities via the remote cloud system 302 and share information with affiliated healthcare entities via the local cloud system 342 and/or the remote cloud system 302. In some examples, the remote cloud system 302 and the local cloud system 342 are hierarchal. For example, the cloud-based clinical information system 100 may allocate or divide tasks, information, etc. between the remote cloud system 302 and the local cloud system 342 based on resources and/or data availability, confidentiality, expertise, content of information, a type of clinical case associated with the information, a source of the information, a destination of the information, and/or or other factors or characteristics. Some example cloud-based clinical information systems do not employ the local cloud system 342.

Figure 4:
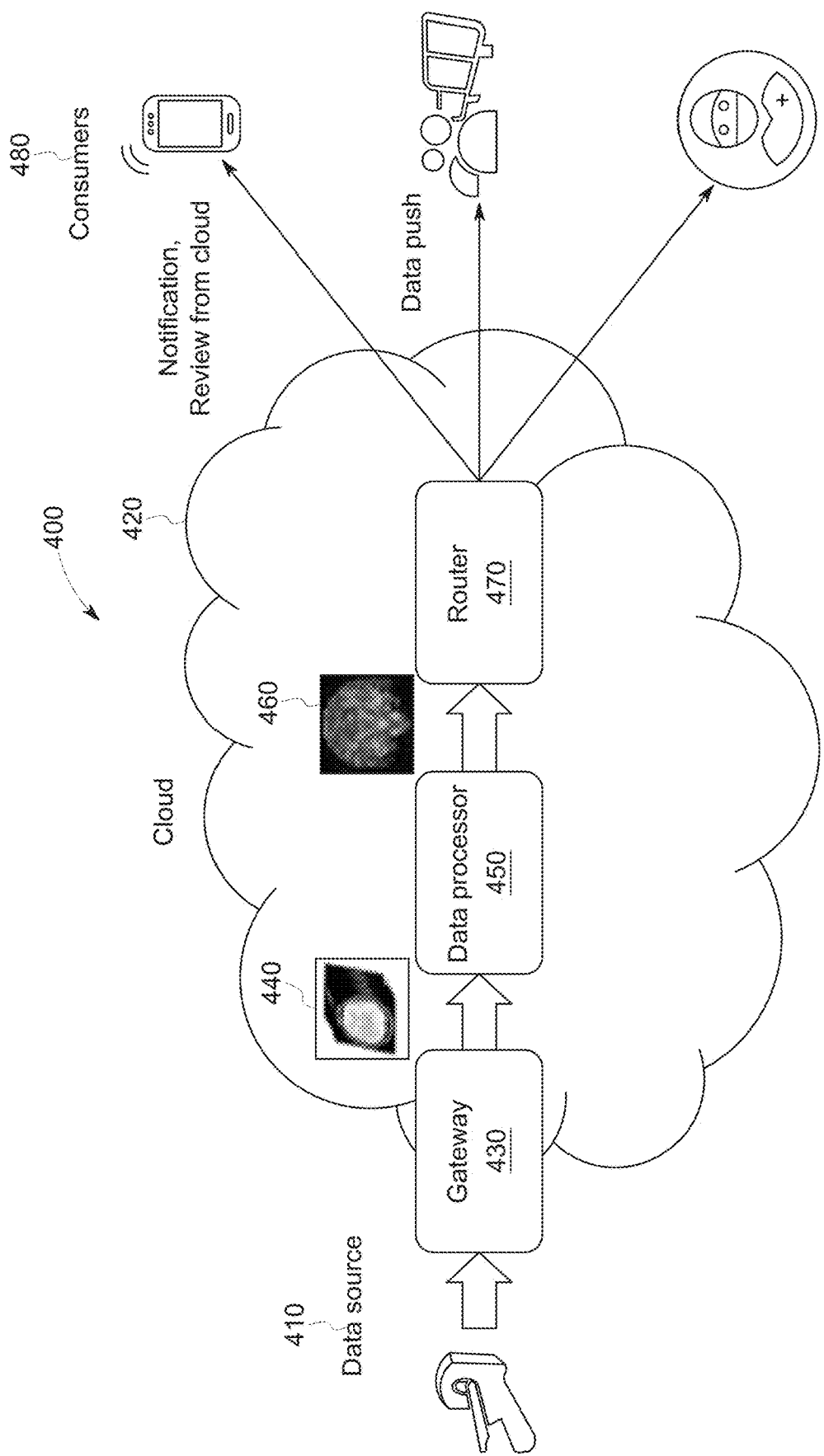
FIG. 4 illustrates a general processing and routing example system.

In certain examples, routing and processing rules are provided to identify, process, and route images from data source(s) to appropriate data consumer(s). FIG. 4 illustrates a general processing and routing example system 400. In the general workflow of the example of FIG. 4, routing and processing workflows are fixed. The processing rules define a set of algorithms to be executed on an input data set. As shown in the example of FIG. 4, a data source 410 provides one or more image data sets 440 to a gateway 430 located in a cloud system 420. The gateway 430 is a bridge between an on-premises network associated with the data source 410 and the cloud system 420. Data from the data source 410 can be driven through the gateway 430 by users and/or automatically pushed according to one or more rules, for example.

The gateway 430 provides the image source data 440 to a data processor 450. Using processing rules, the data processor 450 executes one or more algorithms on the source image data 440 to generate a processed output 460. For example, the data processor 450 executes algorithms for automated creation of parametric maps (e.g., perfusion, diffusion, etc.). The data processor 450 can execute algorithms such as computer aided detection (CAD), image correction (e.g., filtering, motion correction, etc.), and so on. The data processor 450 sends the processed image output 460 to a router 470. The router 470 determines one or more targets to push the processed image data 460 and/or to notify that the processed image data 460 is available.

For example, using routing rules, the router 470 routes the processed image output 460 to one or more data consumers 480. For example, a notification can be sent to allow a user to review the processed image output 460 from a mobile device via the cloud 420. As another example, the processed image output case can be pushed to one or more output devices for viewing, further processing, etc. Routing can be based at least in part on routing elements in the data sets, dispatching logic, identification of patients, procedures, scheduling inside a workgroup, referring physicians, etc.

Pushing data can be efficient when data is eventually consumed on a selected target, for example. This strategy can be pursued when the data should not remain in the Cloud 420, for example. Additionally, the target consumer 480 may be more efficient at interacting with the processed image data 460. For example, dedicated workstations offer higher interactive performance compared to remote review from the cloud 420. Automatically pushing large data sets can save clicks and workflow disruption to users, for example.

Figure 5:
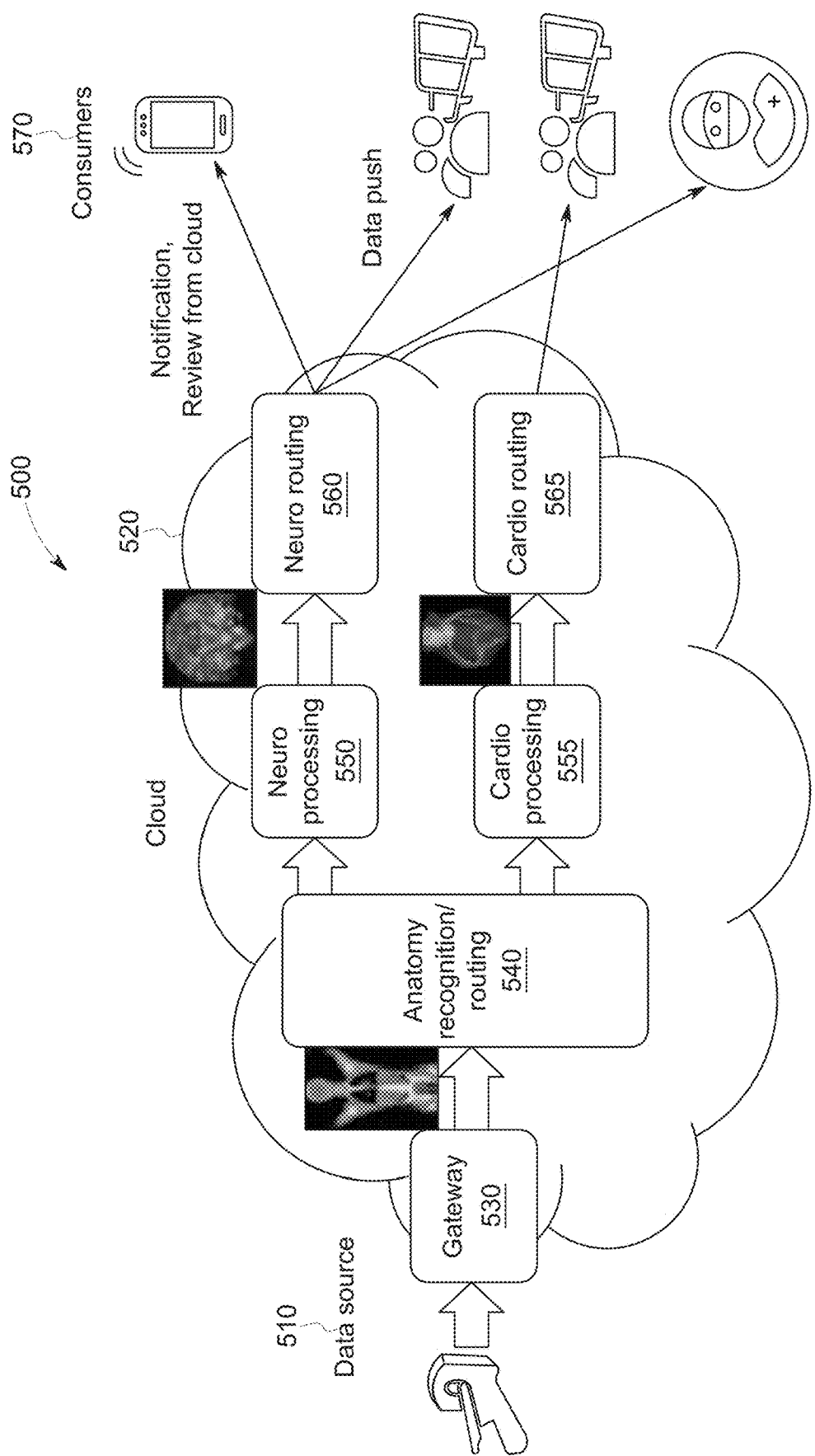
FIG. 5 illustrates an example intelligent routing and processing cloud-based system.

In the example of FIG. 5, however, intelligent, rather than fixed, routing and processing is provided via an example cloud-based system 500 to provide enhanced processing, routing, and storage of image data. As shown in the example of FIG. 5, a data source 510 provides one or more image data sets to a gateway 530 located in a cloud infrastructure 520. The gateway 530 (e.g., an edge device) is a bridge between an on-premises network associated with the data source 510 and the cloud infrastructure 520. Data from the data source 510 can be driven through the gateway 530 by users and/or automatically pushed according to one or more rules, for example.

The gateway 530 provides image source data to an anatomy and procedure recognition and routing processor 540. The anatomy and procedure recognition and routing processor 540 first performs an automatic detection of the anatomy.

Anatomic detection can be executed automatically by the processor 540 based on identification of specific tags (e.g., metadata tags identifying the nature of a series, components of an image, etc.) and/or by detecting image features in the image data. For example, tags can include a series description (e.g., a comment entered to annotate a group of images during scan), a protocol code (e.g., an image metadata that identifies the specific scan parameters and, in many cases, also includes some reference to the anatomy being scanned, etc.), a contrast flag to identify use of a contrast agent, etc.

For example, an image processing approach relies on identifying a number of features (e.g., an amount of bone in a computed tomography (CT) slice and/or one or more complex metrics such as texture analysis, spatial moments and/or other known shape descriptors that may be calculated from edge-detection maps so that they are independent from the acquisition technique) and/or landmarks in the source image data and matching identified features/landmarks to features and/or landmarks labeled in reference templates made available to the recognition processor 540. In a CT context, for example, image features include detecting lungs from a large ratio of voxels in a certain range of values identifying lung tissues, identifying the aorta as a large (e.g., size is within a known range) homogeneous circular area of voxels in a range associated to contrast agent, identifying the liver as the largest area of tissues within the range associated to parenchyma, detecting vertebrae from their location relative to the pelvic area, etc.

Elements of a complex metric build a "feature vector" which feeds a decision engine that computes the most probable anatomy based on classification from training examples or sets of rules. This analysis is also correlated to neighboring locations to determine the most realistic overall anatomy. As a simple example, finding the skull between the neck and the chest or the heart far to the lungs is not very likely.

Several levels of identification can be implemented based on the nature of the input image data. For example, in a cardiology example, cardiac acquisitions including a time element can be processed and/or routed differently from static exams (e.g., not having a time component). Based on an anatomy identified in the input image data, additional elements are added to determine which processing to apply to the image data and a routing strategy for the image data. In certain examples, such as neurology or cardiology, the processor 540 can "guess" or infer an application or clinical use case such as perfusion, vascular processing, etc., rather than, or in addition to, identifying a particular anatomy such as neck, pelvis, etc.

In certain examples, routing may not be performed on the entire image data set. Rather, the processor 540 can separate an image acquisition volume into different anatomical regions, and each of the anatomical regions can be processed separately.

For example, based on the anatomy and procedure recognition processing of the processor 540, a subset of relevant algorithm(s) is selected from a plurality of available algorithms. Many algorithms are specific to a certain type of anatomy, lesion, etc. The example of FIG. 5 illustrates the examples of Neurology and Cardiology. The recognition processor 540 selects a subset of relevant algorithms. In some examples, the processor 540 adds one or more landmarks and/or bounding boxes to help initialize the selected algorithm(s). In some examples, selection of processing to be applied can also be done through virtual routing.

The anatomy recognition processor 540 also develops a routing strategy for the image data. The routing strategy can be used upstream before processing as a "virtual" routing strategy to activate different types of automated processing and/or other tasks in the processing flow, for example. In this mode, images are routed to a specialized "Neurology Processor" when relevant (e.g., with the identified anatomy in the input image data is neurology-related) in the example of FIG. 5. Processed results can be stored in different "folders", displayed, and/or hardcopied according to the determined routing strategy.

The routing strategy can also be applied "downstream" after processing of the image data. Different users and/or target systems can be identified as routing targets based on the identified anatomical application area (e.g., neurology, cardiology, etc.) and/or inferred type of anatomy application and/or clinical use case (e.g., perfusion, vascular processing, etc.). For example, specialized experts (e.g., Neurologists and Cardiologists in the example of FIG. 5), separate referring departments, etc., can be specified as target system recipients of processed image data.

In certain examples, anatomy recognition by the processor 540 can split a data set into sub-regions that are routed and processed separately. For example, a whole body scan or other image that includes several anatomical regions (e.g., Head, Thorax, Abdomen, Pelvis, Extremities, etc.) can be divided into sub-regions that are routed and processed separately.

Based on an outcome of the anatomy recognition processing, the processor 540 routes the input image data to a corresponding anatomy processor. For example, as demonstrated in the example of FIG. 5, identification of a brain and/or nervous system by the recognition processor 540 in the image data set triggers the processor 540 to route the image data for neurology processing 550. Conversely, identification of a heart and/or vascular system by the recognition processor 540 in the image data set triggers the processor 540 to route the image data for cardiology processing 555.

In the example of FIG. 5, neuro processing 550 can include automatic identification of specific anatomical planes and/or landmarks (e.g., mid-sagittal plane, optic nerve, brain structures, etc.). Neuro processing 550 in the example can also include diffusion, perfusion maps, automated skull removal for computed tomography (CT) vascular display, automated measurement of activity inside regions defined from an atlas and/or template, etc.

In the example of FIG. 5, cardio processing 555 can include automatic identification of coronary vessels, myocardium, aorta for CT and magnetic resonance (MR) data sets. Cardio processing 555 in the example can also include image-based motion correction to supplement gating strategies based on electrocardiogram (ECG) data, motion identification for cardiac function, flow analysis, volumetric calculation for cardiac cavities, size calculations for vessels, etc.

Based on the determined processing (e.g., neuro processing 550 or cardio processing 555 in the example of FIG. 5), a router (e.g., neuro router 560 or cardio router 565 in the example of FIG. 5) is selected. A set of systems to which a handle/notification and/or processed data (e.g., images, results, etc.) are sent is further selected based on consideration of the anatomy that has been identified by the recognition processor 540.

For example, different expert systems (and their associated users) and/or other data consumers 570 can be notified and/or processed image data cases can be pushed to different folders based on identified anatomy. If data is pushed to a target system, for example, processed image data and/or results are sent to the target system for further use at the target system. If a notification and/or handle is sent to the target system which can then be used to retrieve data from the cloud 520 on demand.

Data can be pushed, for example, to send large data sets to dedicated review systems (e.g., PACS consoles, radiology workstations, etc.). A notification/handle can be used, for example, to facilitate access from mobile systems (e.g., tablets, smartphones, laptops, etc.) and/or for review using a Web-based client and/or other remote interaction devices.

Figure 6:
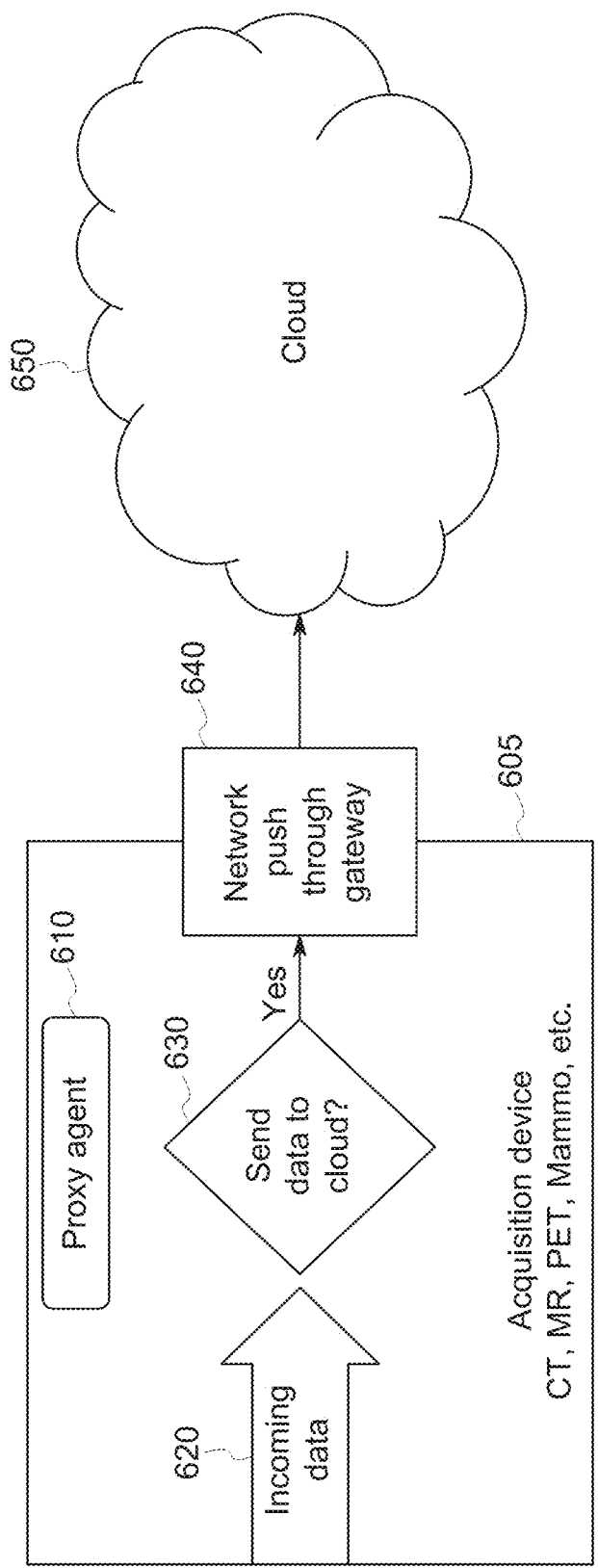
FIG. 6 illustrates an example data flow diagram for providing incoming data from an acquisition device to a cloud.

FIG. 6 illustrates an example data flow diagram for providing incoming data from an acquisition device 605 to a cloud 650. The example acquisition device 605 (e.g., CT, MR, positron emission tomography (PET), mammography, etc.) includes a proxy agent 620 which receives incoming data (e.g., image data) 620 and evaluates the data 620 to determine whether the data is to be sent to the cloud 650 (e.g., is the data authorized for release to affiliated/unaffiliated systems via the cloud 650, is the data large and better suited for cloud 650 storage, is the data to be accessible from a plurality of mobile devices via push and/or pull from the cloud 650, etc.).

For example, data can be deemed suitable to be sent to the cloud 650 based on one or more rules including modality (e.g., CT, MR, mammo, PET, etc.), routing information (e.g., embedded by an imaging scanner in the image data, etc.), series description (e.g., perfusion, cardiac, etc.), size (e.g., send only a largest series in an image data set, etc.), protocol field (e.g., protocol fields identifying neuro, cardiac acquisitions, etc.), presence of Digital Imaging and Communications in Medicine (DICOM) fields identifying a specific acquisition, etc. Information sent to the cloud 650 can include, in addition to the image data, identification of the proxy agent 610 and additional information added from the proxy 610, for example.

If the data is not to be sent to the cloud 650, then the data can be stored locally at the acquisition device 605 and/or locally connected storage. If the data is to be sent to the cloud 650, the data is pushed 640 over a network though a gateway to the cloud 650.

In an example involving CT cardiology imaging and associated workflow, CT image data should only be uploaded to the cloud 650 if the modality is CT. Other modalities are not passed through to the cloud 650 in the CT cardiology workflow. Additionally, data should be pushed to the cloud 650 if the acquisition is gated from an EKG and has cardiac phase information. Data lacking EKG gating and cardiac phase information may not be provided to the cloud 650 in this example. Further routing criteria in the CT cardiology workflow example can include determining that an image series associated with the data is the largest image series in the data set. Key word(s) and/or identifier(s) in the data can also be used to determine whether the data is to be uploaded to the cloud 650 (e.g., a series description includes the word "cardiac", a DICOM protocol identifier is within a white list (an allowed list), etc.).

Figure 7:
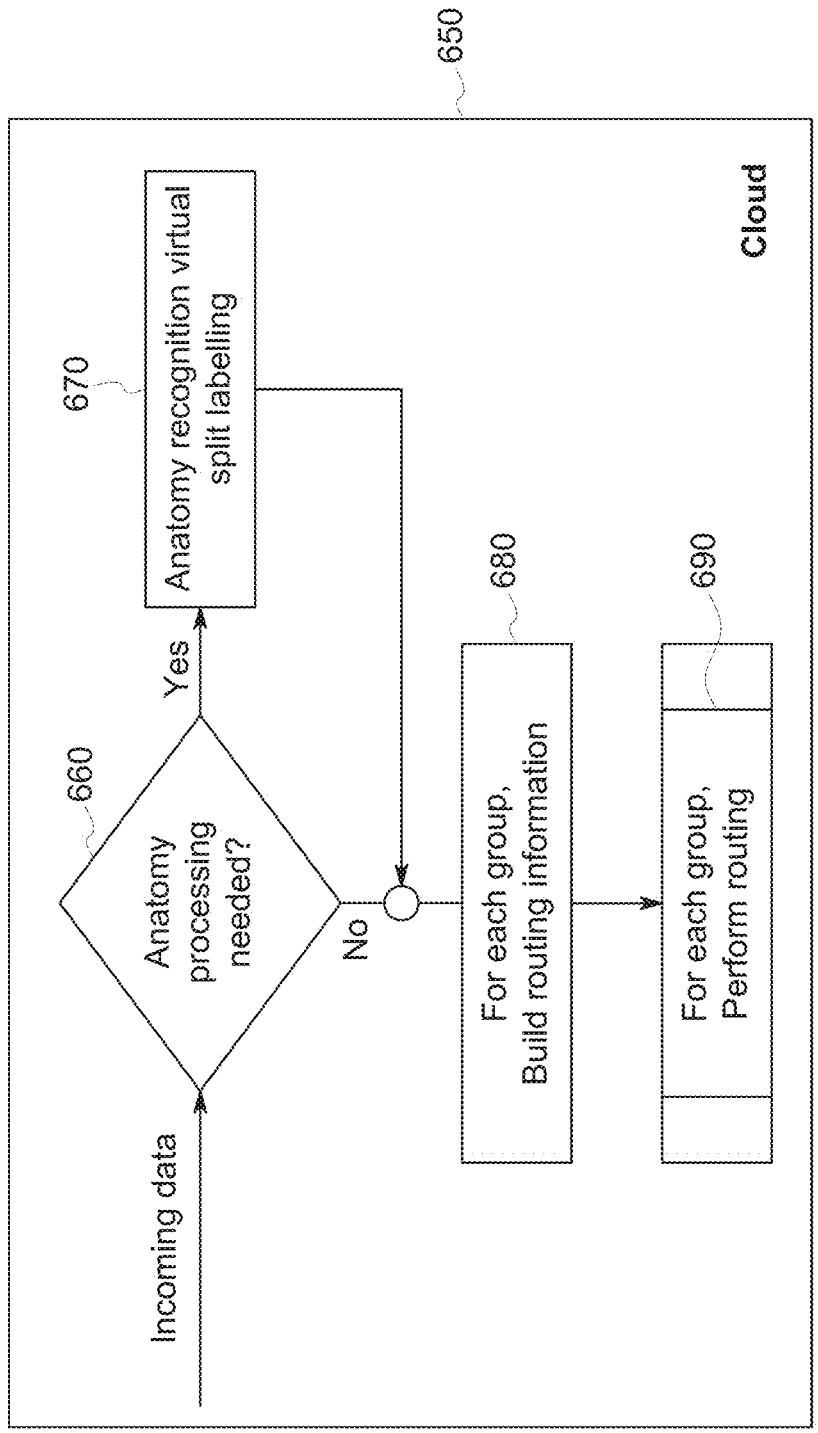
FIG. 7 illustrates an example data flow for routing data in a cloud.

FIG. 7 illustrates an example data flow for routing data in a cloud 650. For example, incoming data from the acquisition device 605 is provided to the cloud 650, which evaluates the data to determine, at block 660, whether anatomy processing is needed to understand and route the incoming data. If anatomy processing is warranted, then, at block 670, anatomy recognition is performed using virtual split, labeling, etc. Following anatomy recognition processing, routing information is built, at block 680, for each group or subset of images. If anatomy processing is not warranted, then, at block 680, routing information is built for each group based on the incoming data without anatomy recognition.

Routing information is a set of routes providing a path for data to a target system, for example. Each route is a sequential list of nodes through or to which a data set is sent and/or notifications are dispatched. Multiple routes can be applied to a data set, potentially simultaneously (or substantially simultaneously given a processing and/or transmission delay, for example).

Nodes can include non-terminal processing nodes and terminal "storage" nodes, for example. Non-terminal processing nodes process input data sets to generate results (e.g., transformed images, measurements, findings, etc.) that are sent to a next node in the route. Processed results can be sent to multiple routes, for example. Terminal storage nodes are destination nodes at which a data set becomes available to one or more target data consumers. Terminal nodes can include cloud storage, workstation, PACS, etc. Notifications are messages dispatched to a certain target (e.g., a user terminal, smart phone, etc.). Then, at block 690, based on the routing information, routing of the data is performed for each group.

Figure 8:
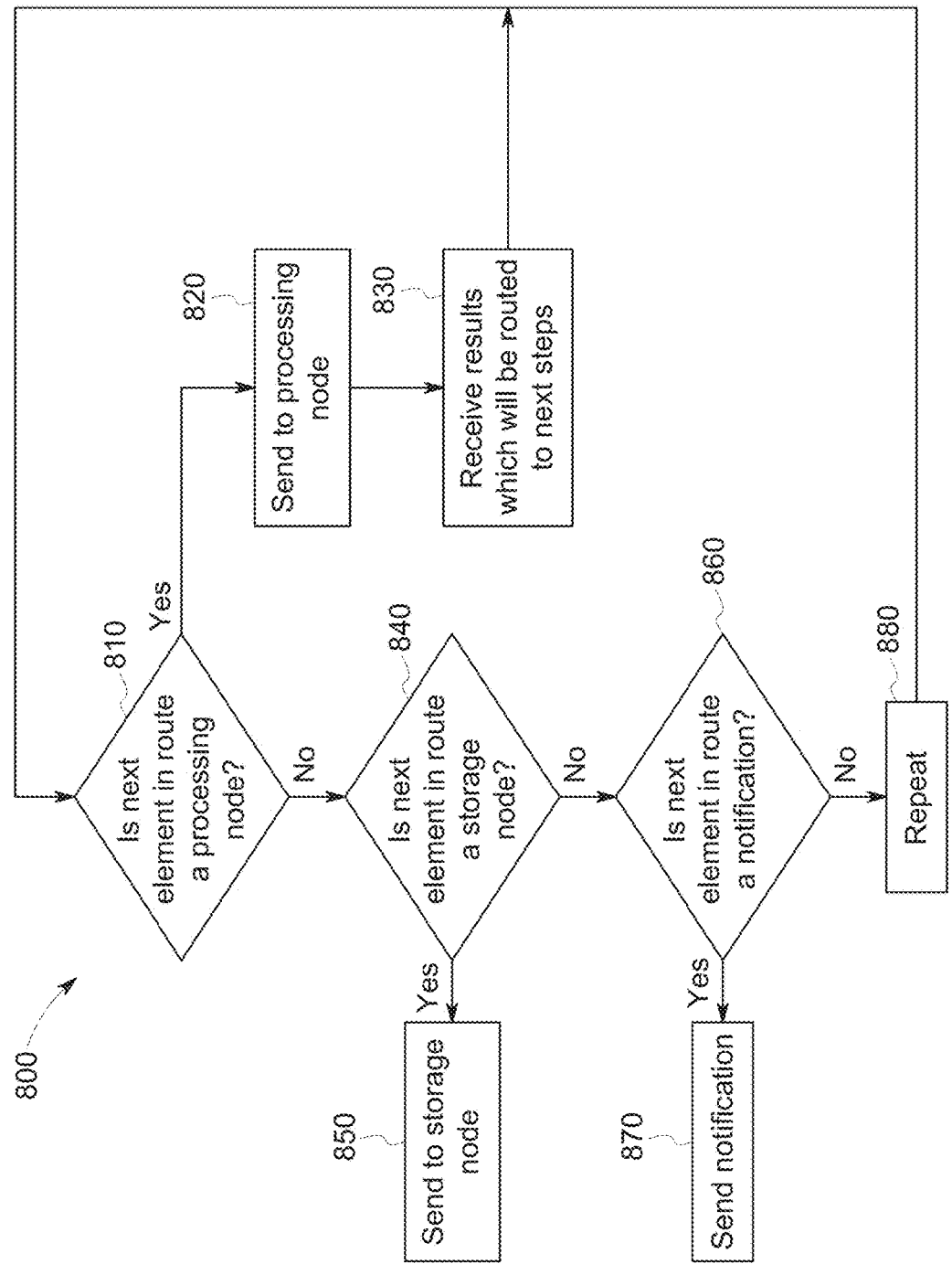
FIG. 8 illustrates an example routing data flow for image data to be sent to a target system via the cloud.

FIG. 8 illustrates an example routing data flow 800 for image data to be sent to a target system via "the cloud". At block 810, a processor, such as the recognition and routing processor 540, determines whether a next element in a determined route for incoming data is a processing node (e.g., rather than a terminal storage node). If the next element in the route for the incoming data is a processing node, then, at block 820, the data is sent to the processing node. After the incoming data is processed by the processing node, then, at block 830, results of the processing are received and can be routed to a next element in the routing plan (e.g., returning to block 810 for further routing of results). In certain examples, data can be sent along several routes to a plurality of processing nodes simultaneously to perform distributed or parallel execution of several processing tasks.

If the next element in the route for data is not a processing node, then, at block 840, the next element in the routing plan is evaluated to determine whether the element is a storage node. If so, then, at block 850, the data is sent to the storage node for storage. If, however, the next element is not a storage node, then, at block 860, the element is analyzed to determine whether the element is a notification. If the next element is a notification, then, at block 870, a notification is sent based on the incoming data. If the next element is not a notification, then, at block 880, the routing repeats at block 810.

Figure 9:
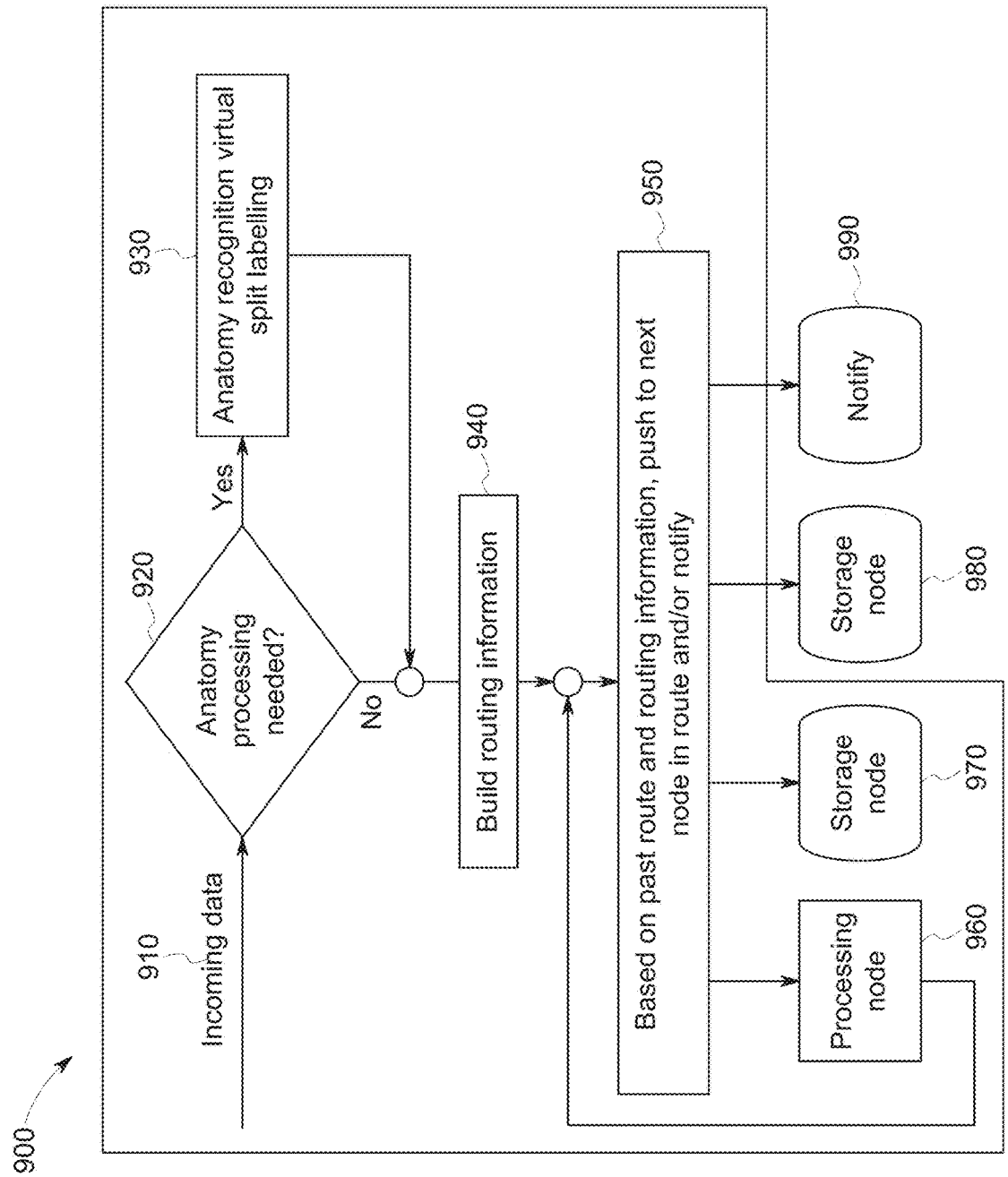
FIG. 9 illustrates a cardiac example of routing in the cloud.

FIG. 9 illustrates a cardiac example of routing in the cloud (e.g., the cloud 520, 650, etc.). As shown in the example of FIG. 9, incoming data 910 is evaluated at block 920 to determine whether anatomy processing is warranted for the incoming data 910. In certain examples, a rule to determine whether anatomy processing is warranted can include, for heart acquisition data in the example of FIG. 9, an analysis of the incoming data 910 to determine whether vertical coverage exceeds an average cardiac height by a set percentage. If the vertical coverage in the incoming data 910 is lower than the average cardiac height, given the set percentage, then the anatomy in the incoming 910 is inferred to be heart data only.

If anatomy processing is needed (e.g., the incoming data is not already identified as cardiac data), then, at block 930, anatomy recognition is generated from the incoming image data 910. Anatomy processing can include anatomy recognition, virtual split, labeling, etc. A processor, such as the recognition and routing processor 540, can then perform anatomy recognition in the example of FIG. 9 by isolating a cardiac region for specific processing and/or detecting acquisitions including a complete aortic section, for example.

In certain examples, anatomy recognition attaches an anatomy label to each slice in a data set. The anatomy label is a combination of an anatomical location (e.g., head, neck, chest, abdomen, cardiac, limbs, spine, etc.) and slice contents (e.g., a determination of which organs are present, which translates into an identification of which applications and/or processing can be applied to the image data set).

Groups (e.g., subsets) of images can be extracted (e.g., a virtual split) to be routed separately. An image group is a set of images sharing a label set assigned through the anatomy recognition. For example, a group may be formed by extracting a heart region from a larger gated acquisition so that a cardiac analysis package processes the extracted heart region in a specific way (e.g., extracting coronaries, etc.). As another example, an image group may be formed by extracting a lung region from complete Thorax Abdomen Pelvis cases.

At block 940, whether or not anatomy processing has been conducted, routing information is built (e.g., based on the incoming data 910 and/or anatomy processing information, etc.). For a cardiac region, for example, routing includes building a route including a coronary identification and quantification processor (e.g., General Electric's Advantage Workstation™, etc.), pushing results to a local PACS, sending a notification to radiologist A's smart phone that the results are available, etc. For a larger region including an aorta, for example, a route includes instructions to send data to a processor which detects an upper aorta to extract a mitral valve location, send data to a processor which detects and quantifies aorta and iliac vessels to provide size a assessment for valve procedure, and push results to Radiologist A's workstation for quality control, etc.

At block 950, based on past route and routing information, data is pushed to a next node in the route and/or a notification is generated. Thus, for example, data can be pushed to a processing node 960 for data processing (e.g., anatomy-based processing, etc.), pushed to a storage node 970, 980 for storage, used to generate a notification 990, etc.

Figure 10:
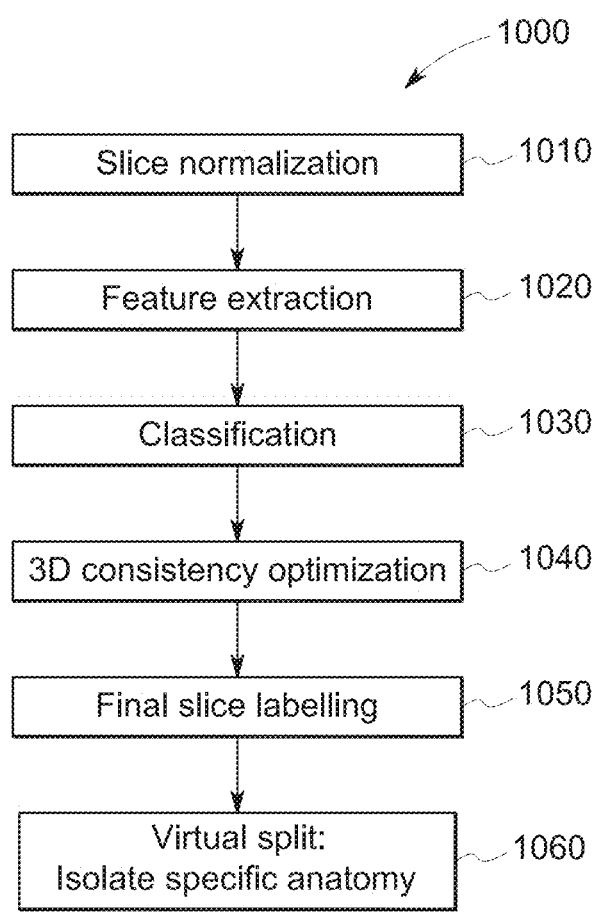
FIG. 10 illustrates an example method for anatomy recognition to be applied by a processor in the cloud.

FIG. 10 illustrates an example method for anatomy recognition to be applied by a processor (e.g., processor 540) in the cloud (e.g., cloud 520, 650, etc.). At block 1010, image slices in an incoming image data set are normalized. For example, image slices can be adjusted to a center position (e.g., using moments, etc.). As another example, a grey level histogram can be normalized in the image slices (e.g., MR image slices, etc.).

At block 1020, features are extracted from the normalized image slices. For example, a feature vector can be computed from the image data based on a combination of a histogram analysis, grey-level moments, etc.

At block 1030, the extracted feature vector is classified. For example, the extracted feature vector can be classified using a Random Forest classifier.

At block 1040, three-dimensional (3D) consistency is optimized. For example, a 3D consistency check is applied between image slices to confirm that, for example, a neck is always lower than a head in an image.

At block 1050, final slice labeling is applied. For example, anatomy information (e.g., heart, lung, brain, etc.) is attached to each image slice.

At block 1060, a virtual split is derived. For example, smaller sets for specific anatomy and/or processing are isolated. For example, in an image data acquisition including check and neck, a heart region is selected for cardiac processing, and the head/neck are isolated for vascular processing. Thus, anatomy can be recognized and subdivided or split for separate further processing and routing.

Figure 11:
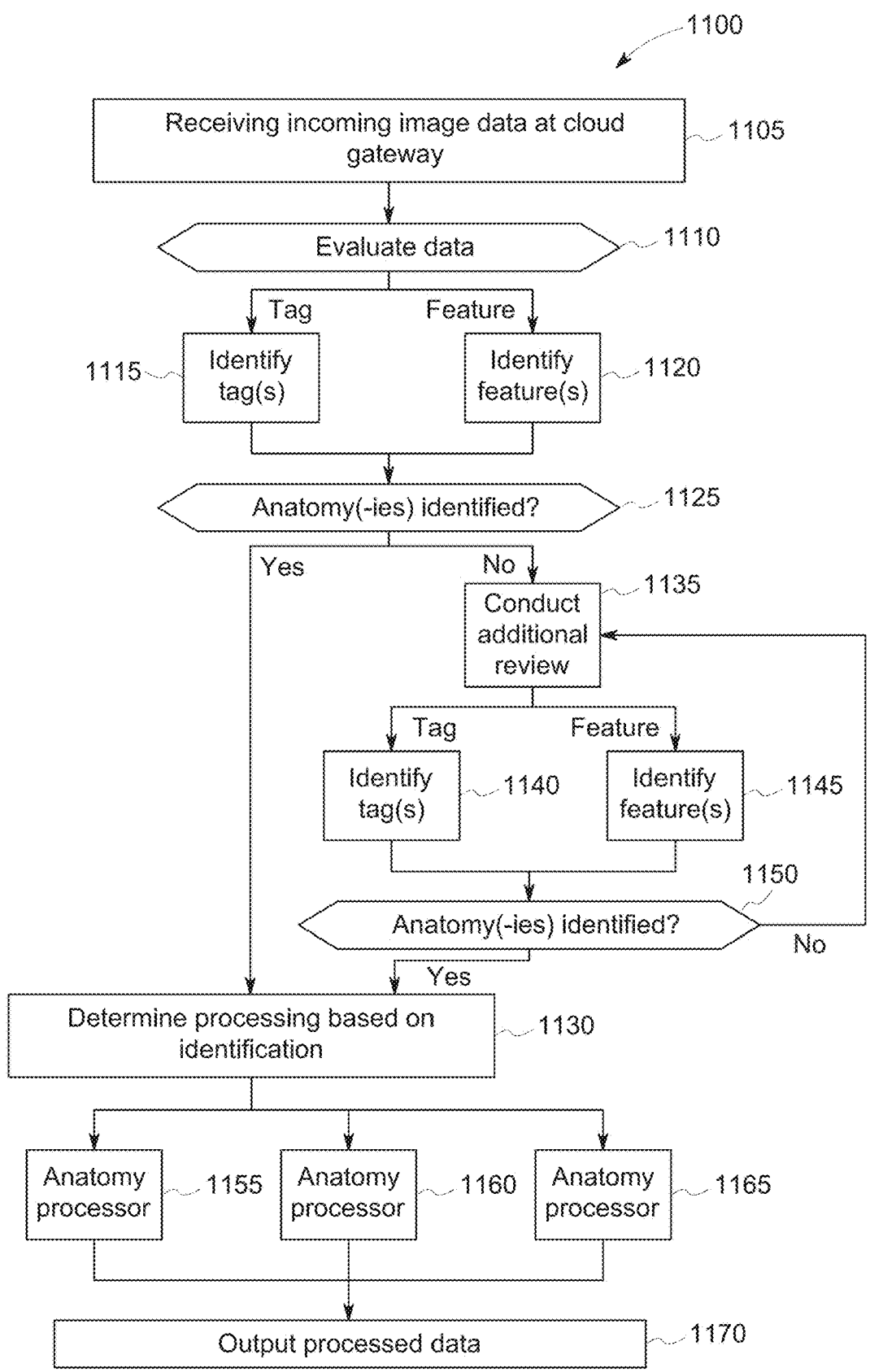
FIG. 11 illustrates a flow diagram of an example process for intelligent processing and routing of image data.

FIG. 11 illustrates a flow diagram of an example process 1100 for intelligent processing and routing of image data. At block 1105, incoming image data is received at a cloud gateway. At block 1110, the image data is evaluated by an anatomy processor in the cloud which detects whether one or more tags are present in the image data and/or whether image features are to be detected in the image data.

If one or more tags are detected in the image data, then, at block 1115, the image data is evaluated to identify tags. If the image data is to be evaluated for image feature detection, then, at block 1120, the image data is evaluated to identify one or more anatomical features in the image data.

At block 1125, the image evaluation is analyzed to determine whether anatomy(-ies) have been identified in the image data based on the tag(s) (block 1115) and/or image feature analysis (block 1120). If anatomy(-ies) have been identified for further processing and routing, then, at block 1130, relevant processing is determined based on the identified anatomy(-ies).

If, however, further evaluation is warranted to identified anatomy(-ies) in the image data, then, at block 1135, an additional review is conducted to identify whether further tag(s) and/or image feature(s) are to be evaluated. Based on that review, the image data is re-evaluated for tag(s) (block 1140) and/or image feature(s) (block 1145), and, at block 1150, the image evaluation is analyzed to determine whether anatomy(-ies) have been identified in the image data based on the tag(s) (block 1140) and/or image feature analysis (block 1145). If further evaluation is warranted, then the loop repeats back to block 1135. If, however, anatomy(-ies) have been identified in the image data for further processing and routing, then, at block 1130, relevant processing is determined based on the identified anatomy(-ies). Processing may be determined, for example, based on identification of neurologic anatomy, cardiac anatomy, circulatory anatomy, abdominal anatomy, respiratory anatomy, digestive anatomy, etc.

Based on anatomy, the image data (or a certain anatomical portion thereof) is routed to one of a plurality of available anatomy processors 1155, 1160, 1665, etc. (three shown here for purposes of illustration only). For example, cardiac data is routed to a cardiac processor 1155, neurologic data is routed to a neurology processor 1160, respiratory data is routed to a respiratory processor 1165, etc. The anatomy processors 1155-1165 can be implemented using a plurality of particularly programmed virtual machines, physical processors, and/or customized circuitry, for example. The anatomy processors 1155-1165 apply particular algorithm(s) according to particular rule(s) based on the type of anatomy identified in the image and/or image portion that is routed to that processor 1155-1165.

At block 1170, processed image data is provided for output from one or more of the applicable anatomy processors 1155-165. Processed data can be output for display, storage, routing to a clinical application and/or system, used in a notification, etc.

Figure 12:
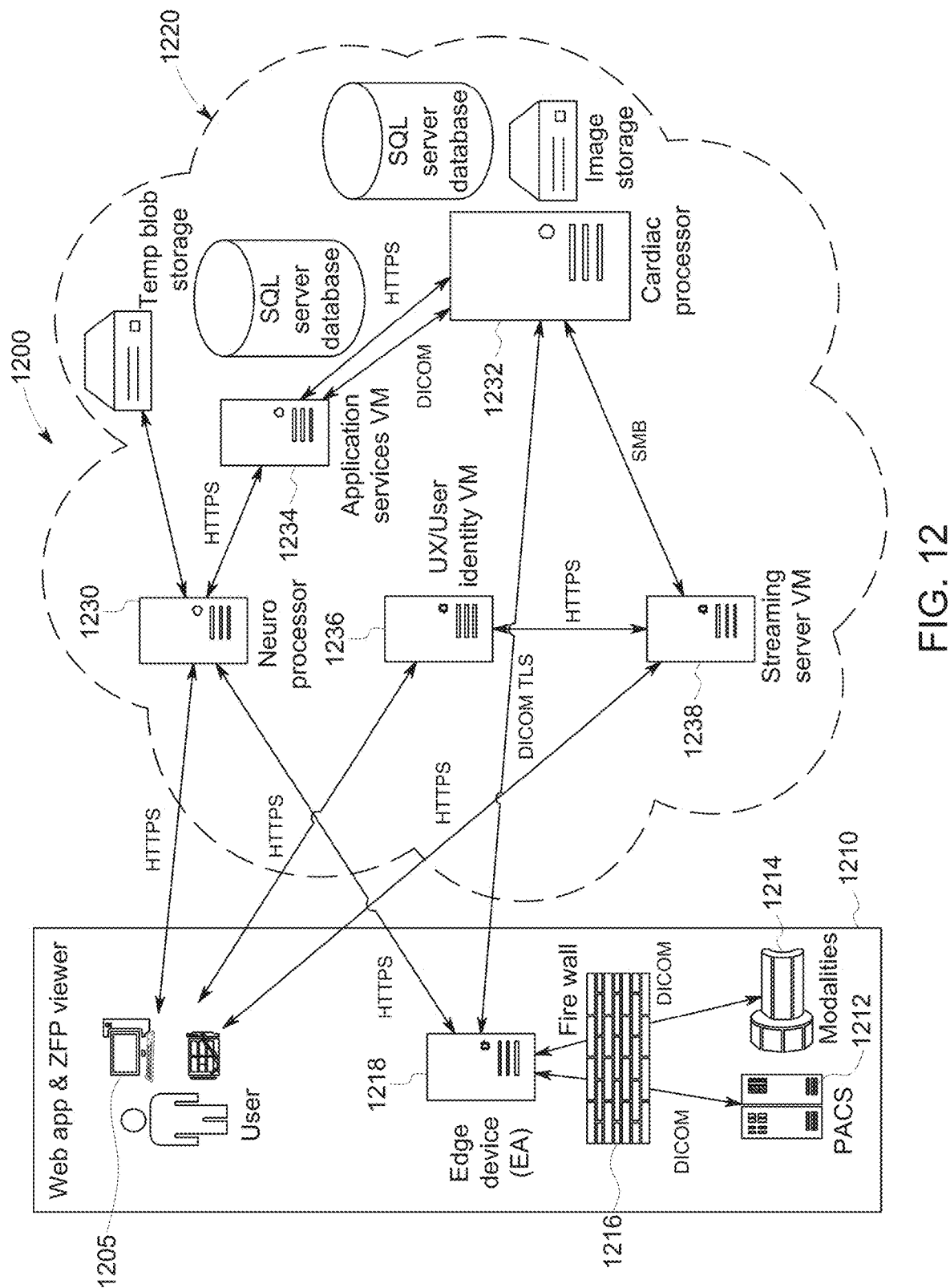
FIG. 12 illustrates an example architecture that may be used to implement an example intelligent cloud-based processing and routing system.

FIG. 12 illustrates an example implementation of an example cloud-based image data processing and routing system 1200, such as a system used to execute the method of FIG. 11. In the illustrated example of FIG. 12, the system 1200 includes a data source 1210 and a cloud infrastructure 1220. The example data source 1210 includes a workstation 1205 (e.g., a Web-based application and zero footprint (ZFP) viewer, etc.), image storage (e.g., PACS, etc.) 1212, and one or more imaging modalities (e.g., x-ray, CT, MR, ultrasound, PET, etc.) 1214. The image storage 1212 and/or modality(-ies) 1214 communicate with the cloud 1220 via an edge device 1218, which serves as a gateway between the data source 1210 and the cloud infrastructure 1220, for example. The devices 1212, 1214 may communicate with the edge device 1218 through a firewall 1216, for example. In some examples, the firewall 1216 may be absent. In some examples, a user can also access the cloud infrastructure 1220 via the workstation 1205.

Via the cloud infrastructure 1220, the workstation 1205 and/or (via the edge device 1218) devices 1212, 1214 can access one or more processors hosted in the cloud 1220. For example, a neuro processor 1230, a cardiac processor 1232, etc., can be provided in the cloud infrastructure 1220 to process relevant subset(s) of image data based on identified anatomy in such image data. Additionally, the cloud infrastructure can provide a user experience (UX) and/or user identity virtual machine (VM) 1236 to support user identification, authentication, authorization, and/or customization, for example. The cloud infrastructure 1220 can also provide one or more supportive VMs/processors such as an application services VM 1234, a streaming server VM 1238, data storage, etc.

Figure 13:
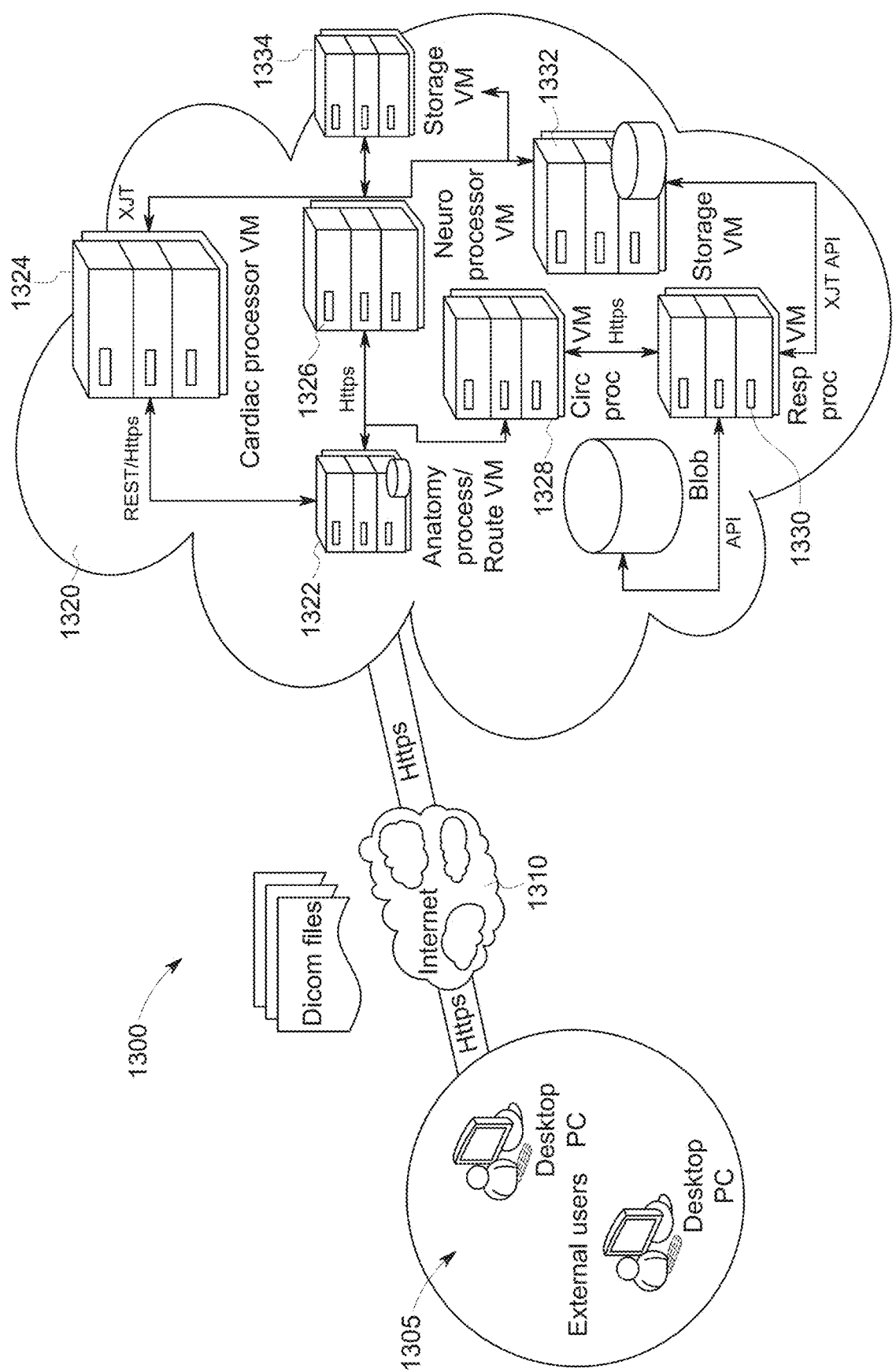
FIG. 13 illustrates an example architecture that may be used to implement an example intelligent cloud-based processing and routing system.

FIG. 13 illustrates another example implementation of an example cloud-based processing and routing system 1300. In the illustrated example, a plurality of healthcare entities 1305 are in communication with the cloud 1320 via the internet 1310. The example cloud 1320 includes an anatomy process/route VM 1322, which communicates with a plurality of other VMs configured in the cloud 1320. As disclosed above, based on one or more anatomy(-ies) identified in incoming image data, the anatomy process/routing VM 1322 routes image data to one or more VMs such as a cardiac processor VM 1324, a neurology processor VM 1326, a circulatory processor VM 1328, a respiratory processor VM 1330, one or more storage VMs 1332, 1334, etc.

Flow diagrams representative of example machine readable instructions for implementing the example cloud-based systems 100, 200, 400, 500, 650, 1200, 1300 are shown in FIGS. 6-11. In these examples, the machine readable instructions comprise a program for execution by a processor such as the processor 1412 shown in the example processor platform 1400 discussed below in connection with FIG. 14. The program may be embodied in software stored on a tangible computer readable storage medium such as a CD-ROM, a floppy disk, a hard drive, a digital versatile disk (DVD), a Blu-ray disk, or a memory associated with the processor 1412, but the entire program and/or parts thereof could alternatively be executed by a device other than the processor 1412 and/or embodied in firmware, dedicated hardware, and/or virtual processor/machine. Further, although the example programs are described with reference to the flowcharts illustrated in FIGS. 6-11, many other methods of implementing the example cloud-based systems 100, 200, 400, 500, 650, 1200, 1300 may alternatively be used. For example, the order of execution of the blocks may be changed, and/or some of the blocks described may be changed, eliminated, or combined. In certain examples, programs can be linked to streams of messages managed and dispatched by queue engines in a cloud-based system.

As mentioned above, the example processes of FIGS. 6-11 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of FIGS. 6-11 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

While an example manner of implementing the cloud-based systems 100, 200, 400, 500, 650, 1200, 1300 are illustrated in FIGS. 1-5 and 12-14, one or more of the elements, processes and/or devices illustrated in FIGS. 1-5 and 12-14 may be combined, divided, re-arranged, omitted, eliminated and/or implemented in any other way. Further, example components of the systems 100, 200, 400, 500, 650, 1200, 1300 may be implemented by hardware, software, firmware and/or any combination of hardware, software and/or firmware. Thus, for example, components of the example system 100, 200, 400, 500, 650, 1200, 1300 can be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the components of example systems 100, 200, 400, 500, 650, 1200, 1300 is/are hereby expressly defined to include a tangible computer readable storage device or storage disk such as a memory, a digital versatile disk (DVD), a compact disk (CD), a Blu-ray disk, etc. storing the software and/or firmware. Further still, the example cloud-based system 100, 200, 400, 500, 650, 1200, 1300 may include one or more elements, processes and/or devices in addition to, or instead of, those illustrated in FIGS. 1-5 and 12-14, and/or may include more than one of any or all of the illustrated elements, processes and devices.

Figure 14:
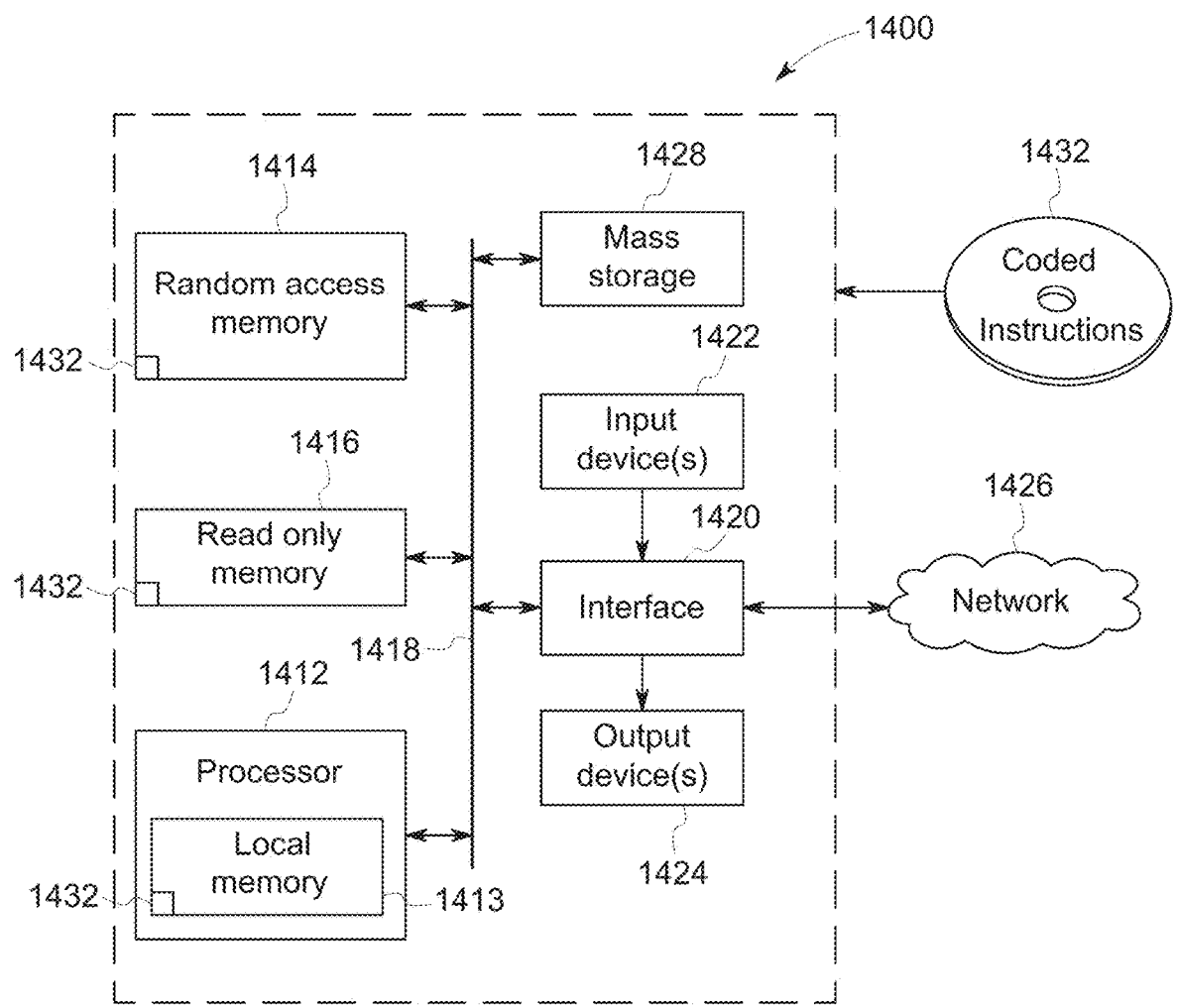
FIG. 14 is a block diagram of an example processor platform that may be used to implement the example systems and methods disclosed herein.

FIG. 14 is a block diagram of an example processor platform 1400 capable of executing the instructions of FIGS. 6-11 to implement the example system 100, 200, 400, 500, 650, 1200, 1300 of FIGS. 1-5 and 12-13. The processor platform 1400 can be, for example, a server, a personal computer, a mobile device (e.g., a cell phone, a smart phone, a tablet such as an iPad™), a personal digital assistant (PDA), an Internet appliance, a DVD player, a CD player, a digital video recorder, a Blu-ray player, a gaming console, a personal video recorder, a set top box, or any other type of computing device.

The processor platform 1400 of the illustrated example includes a processor 1412. The processor 1412 of the illustrated example is hardware. For example, the processor 1412 can be implemented by one or more integrated circuits, logic circuits, microprocessors or controllers from any desired family or manufacturer.

The processor 1412 of the illustrated example includes a local memory 1413 (e.g., a cache). The processor 1412 of the illustrated example is in communication with a main memory including a volatile memory 1414 and a non-volatile memory 1416 via a bus 1418. The volatile memory 1414 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1416 may be implemented by flash memory and/or any other desired type of memory device. Access to the main memory 1414, 1416 is controlled by a memory controller.

The processor platform 1400 of the illustrated example also includes an interface circuit 1420. The interface circuit 1420 may be implemented by any type of interface standard, such as an Ethernet interface, a universal serial bus (USB), and/or a PCI express interface.

In the illustrated example, one or more input devices 1422 are connected to the interface circuit 1420. The input device(s) 1422 permit(s) a user to enter data and commands into the processor 1412. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1424 are also connected to the interface circuit 1420 of the illustrated example. The output devices 1424 can be implemented, for example, by display devices (e.g., a light emitting diode (LED), an organic light emitting diode (OLED), a liquid crystal display, a cathode ray tube display (CRT), a touchscreen, a tactile output device, a light emitting diode (LED), a printer and/or speakers). The interface circuit 1420 of the illustrated example, thus, typically includes a graphics driver card, a graphics driver chip or a graphics driver processor.

The interface circuit 1420 of the illustrated example also includes a communication device such as a transmitter, a receiver, a transceiver, a modem and/or network interface card to facilitate exchange of data with external machines (e.g., computing devices of any kind) via a network 1426 (e.g., an Ethernet connection, a digital subscriber line (DSL), a telephone line, coaxial cable, a cellular telephone system, etc.).

The processor platform 1400 of the illustrated example also includes one or more mass storage devices 1428 for storing software and/or data. Examples of such mass storage devices 1428 include floppy disk drives, hard drive disks, compact disk drives, Blu-ray disk drives, RAID systems, and digital versatile disk (DVD) drives.

The coded instructions 1432 of FIG. 14 may be stored in the mass storage device 1428, in the volatile memory 1414, in the non-volatile memory 1416, and/or on a removable tangible computer readable storage medium such as a CD or DVD.

The subject matter of this description may be implemented as stand-alone system or for execution as an application capable of execution by one or more computing devices. The application (e.g., webpage, downloadable applet or other mobile executable) can generate the various displays or graphic/visual representations described herein as graphic user interfaces (GUIs) or other visual illustrations, which may be generated as webpages or the like, in a manner to facilitate interfacing (receiving input/instructions, generating graphic illustrations) with users via the computing device(s).

Memory and processor as referred to herein can be stand-alone or integrally constructed as part of various programmable devices, including for example a desktop computer or laptop computer hard-drive, field-programmable gate arrays (FPGAs), application-specific integrated circuits (ASICs), application-specific standard products (ASSPs), system-on-a-chip systems (SOCs), programmable logic devices (PLDs), etc. or the like or as part of a Computing Device, and any combination thereof operable to execute the instructions associated with implementing the method of the subject matter described herein.

Computing device as referenced herein can include: a mobile telephone; a computer such as a desktop or laptop type; a Personal Digital Assistant (PDA) or mobile phone; a notebook, tablet or other mobile computing device; or the like and any combination thereof.

Computer readable storage medium or computer program product as referenced herein is tangible and can include volatile and non-volatile, removable and non-removable media for storage of electronic-formatted information such as computer readable program instructions or modules of instructions, data, etc. that may be stand-alone or as part of a computing device. Examples of computer readable storage medium or computer program products can include, but are not limited to, RAM, ROM, EEPROM, Flash memory, CD-ROM, DVD-ROM or other optical storage, magnetic cassettes, magnetic tape, magnetic disk storage or other magnetic storage devices, or any other medium which can be used to store the desired electronic format of information and which can be accessed by the processor or at least a portion of the computing device.

The terms module and component as referenced herein generally represent program code or instructions that causes specified tasks when executed on a processor. The program code can be stored in one or more computer readable mediums.

Network as referenced herein can include, but is not limited to, a wide area network (WAN); a local area network (LAN); the Internet; wired or wireless (e.g., optical, Bluetooth, radio frequency (RF)) network; a cloud-based computing infrastructure of computers, routers, servers, gateways, etc.; or any combination thereof associated therewith that allows the system or portion thereof to communicate with one or more computing devices.

The term user and/or the plural form of this term is used to generally refer to those persons capable of accessing, using, or benefiting from the present disclosure.

Technical effects of the subject matter described above can include, but is not limited to, providing cloud-based clinical information systems and associated methods. Moreover, the system and method of this subject matter described herein can be configured to provide an ability to better understand large volumes of data generated by devices across diverse locations, in a manner that allows such data to be more easily exchanged, sorted, analyzed, acted upon, and learned from to achieve more strategic decision-making, more value from technology spend, improved quality and compliance in delivery of services, better customer or business outcomes, and optimization of operational efficiencies in productivity, maintenance and management of assets (e.g., devices and personnel) within complex workflow environments that may involve resource constraints across diverse locations.

This written description uses examples to disclose the subject matter, and to enable one skilled in the art to make and use the invention. Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A method comprising:
    evaluating, automatically using at least a first processor, image data to identify one or more anatomy in the image data by building a feature vector from at least one of image features or tags identified in the image data to compute a probable anatomy identification in comparison to at least one of training examples or rules;
    building, using the at least the first processor, a set of routes to process the image data, each route including one or more nodes, wherein the set of routes includes at least one processing node and at least one storage node, the at least one processing node to include a selected anatomy processor from a plurality of anatomy processors, each of the plurality of anatomy processors configured to process the image data based on a different anatomy, the selected anatomy processor configured to process the image data based on a selected one of the one or more anatomy;
    routing, using the at least the first processor, the image data according to the set of routes to process the image data using at least the selected anatomy processor to generate processed image data; and
    generating, automatically using the at least the first processor or the selected anatomy processor, at least one of a) a push of the processed image data to a data consumer or b) a notification of availability of the processed image data in at least one storage node.

2. The method of claim 1, wherein the at least the first processor is part of a cloud infrastructure.

3. The method of claim 1, wherein at least one storage node is associated with an exam record for the image data.

4. The method of claim 1, wherein the image data is evaluated for routing and processing as the image data is streamed to the at least the first processor.

5. The method of claim 1, wherein the routing is facilitated using at least one anatomy router corresponding to the one or more anatomy identified in the image data.

6. The method of claim 1, wherein the set of routes includes a plurality of routes defined by a plurality of processing nodes and a plurality of storage nodes.

7. The method of claim 1, further including processing, at each processing node, the image data according an anatomy-specific processing algorithm instantiated by the anatomy processor associated with the respective processing node.

8. At least one non-transitory computer-readable storage medium including instructions that, when executed, cause at least one first processor to at least:
    evaluate image data to identify one or more anatomy in the image data by building a feature vector from at least one of image features or tags identified in the image data to compute a probable anatomy identification in comparison to at least one of training examples or rules;

build a set of routes to process the image data, each route including one or more nodes, wherein the set of routes includes at least one processing node and at least one storage node, the at least one processing node to include a selected anatomy processor from a plurality of anatomy processors, each of the plurality of anatomy processors configured to process the image data based on a different anatomy, the selected anatomy processor configured to process the image data based on a selected one of the one or more anatomy;

route the image data according to the set of routes to process the image data using at least the selected anatomy processor to generate processed image data; and generate at least one of a) a push of the processed image data to a data consumer or b) a notification of availability of the processed image data in at least one storage node.

9. The at least one computer-readable storage medium of claim 8, wherein the at least one first processor is part of a cloud infrastructure.

10. The at least one computer-readable storage medium of claim 8, wherein at least one storage node is associated with an exam record for the image data.

11. The at least one computer-readable storage medium of claim 8, wherein the image data is evaluated for routing and processing as the image data is streamed to the at least one first processor.

12. The at least one computer-readable storage medium of claim 8, wherein the routing is facilitated using at least one anatomy router corresponding to the one or more anatomy identified in the image data.

13. The at least one computer-readable storage medium of claim 8, wherein the set of routes includes a plurality of routes defined by a plurality of processing nodes and a plurality of storage nodes.

14. The at least one computer-readable storage medium of claim 8, wherein, at each processing node, the image data is processed according an anatomy-specific processing algorithm instantiated by the anatomy processor associated with the respective processing node.

15. An apparatus comprising:
at least one computer-readable non-transitory storage medium including instructions; and
at least one first processor to at least:
evaluate, by executing an instruction, image data to identify one or more anatomy in the image data by building a feature vector from at least one of image features or tags identified in the image data to compute a probable anatomy identification in comparison to at least one of training examples or rules;
build, by executing an instruction, a set of routes to process the image data, each route including one or more nodes, wherein the set of routes includes at least one processing node and at least one storage node, the at least one processing node to include a selected anatomy processor from a plurality of anatomy processors, each of the plurality of anatomy processors configured to process the image data based on a different anatomy, the selected anatomy processor configured to process the image data based on a selected one of the one or more anatomy;
route, by executing an instruction, the image data according to the set of routes to process the image data using at least the selected anatomy processor to generate processed image data; and
generate, by executing an instruction, at least one of a) a push of the processed image data to a data consumer or b) a notification of availability of the processed image data in at least one storage node.

16. The apparatus of claim 15, wherein the at least one first processor is part of a cloud infrastructure.

17. The apparatus of claim 15, wherein at least one storage node is associated with an exam record for the image data.

18. The apparatus of claim 15, wherein the image data is evaluated for routing and processing as the image data is streamed to the at least one first processor.

19. The apparatus of claim 15, further including at least one anatomy router corresponding to the one or more anatomy identified in the image data to route the image data.

20. The apparatus of claim 15, wherein the set of routes includes a plurality of routes defined by a plurality of processing nodes and a plurality of storage nodes.

* * * * *